US011168325B2

(12) United States Patent
Androsavich et al.

(10) Patent No.: US 11,168,325 B2
(45) Date of Patent: *Nov. 9, 2021

(54) METHODS FOR TREATMENT OF POLYCYSTIC KIDNEY DISEASE

(71) Applicants: Regulus Therapeutics Inc., San Diego, CA (US); Board of Regents of the University of Texas System, Austin, TX (US)

(72) Inventors: John R. Androsavich, San Diego, CA (US); B. Nelson Chau, San Diego, CA (US); Vishal D. Patel, Dallas, TX (US)

(73) Assignees: Regulus Therapeutics Inc., San Diego, CA (US); Board of Regents of The University of Texas System, Austin, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/823,904

(22) Filed: Mar. 19, 2020

(65) Prior Publication Data

US 2020/0231971 A1 Jul. 23, 2020

Related U.S. Application Data

(63) Continuation of application No. 15/753,865, filed as application No. PCT/US2016/048603 on Aug. 25, 2016, now Pat. No. 10,633,657.

(60) Provisional application No. 62/210,031, filed on Aug. 26, 2015.

(51) Int. Cl.
| | | |
|---|---|---|
| C12N 15/113 | (2010.01) | |
| A61K 45/06 | (2006.01) | |
| A61K 31/713 | (2006.01) | |
| A61P 9/12 | (2006.01) | |
| A61P 13/12 | (2006.01) | |

(52) U.S. Cl.
CPC .......... *C12N 15/113* (2013.01); *A61K 31/713* (2013.01); *A61K 45/06* (2013.01); *A61P 9/12* (2018.01); *A61P 13/12* (2018.01); *C12N 2310/113* (2013.01); *C12N 2310/315* (2013.01); *C12N 2310/322* (2013.01); *C12N 2310/3231* (2013.01)

(58) Field of Classification Search
None
See application file for complete search history.

(56) References Cited

U.S. PATENT DOCUMENTS

| 7,683,036 B2 | 3/2010 | Esau et al. |
| 2012/0088902 A1 | 4/2012 | Currie et al. |
| 2012/0115917 A1 | 5/2012 | Toler et al. |

FOREIGN PATENT DOCUMENTS

| JP | 2007-529459 | 10/2007 |
| WO | WO 2018/106566 | 6/1918 |
| WO | WO 2018/106568 | 6/1918 |
| WO | WO 2005/089731 | 9/2005 |
| WO | WO 2007/126150 | 11/2007 |
| WO | WO 2008/042973 | 4/2008 |
| WO | WO 2008/131191 | 10/2008 |
| WO | WO 2015/061684 | 4/2015 |
| WO | WO 2015/123449 | 8/2015 |

OTHER PUBLICATIONS

Carney, "MicroRNA-17: A New Drug Target for ADPKD," Nature Reviews Nephrology, Mar. 6, 2017, 1 page.
Hajarnis et al., "Chapter 13: MicroRNAs and Polycystic Kidney Disease," Brisbane: Codon Publications, Nov. 2015, 13 pages.
Hajarnis et al., "MicroRNA-17 Family Promotes Polycystic Kidney Disease Progression Through Modulation of Mitochondrial Metabolism," Nature Communications, 2017, 8:1-14.
International Search Report received in PCT/US2016/048603, dated Nov. 30, 2016, 17 pages.
Kurschat et al., "An Approach to Cystic Kidney Diseases: the Clinician's View," Nature Reviews, 2014, 10:687-699.
Lakhia et al., "MicroRNA-21 Aggravates Cyst Growth in a Model of Polycystic Kidney Disease," J Am Soc Nephrol, 2015, 27:1-12.
Matsubara et al., "Apoptosis Induction by Antisense Oligonucleotides Against miR-17-5p and miR-20a in Lung Cancers Overexpressing miR-17-92," Oncogene, 2007, 26(41):6099-6105.
NIH Grant 1R01DK102572-01A1, "MicroRNAs: New Regulators of Disease Progression in Polycystic Kidney Disease," Awarded May 11, 2015, downloaded Feb. 20, 2018, 2 pages.
NIH Grant 1R03DK099568-01, "Mirna Based Therapeutics in Polycystic Kidney Disease," Awarded Jul. 19, 2013, downloaded Feb. 20, 2018, 2 pages.
NIH Grant 5R01DK102572-02, "MicroRNAs: New Regulators of Disease Progression in Polycystic Kidney Disease," Awarded May 2, 2016, downloaded Feb. 20, 2018, 2 pages.
NIH Grant 5R01DK102572-03, "MicroRNAs: New Regulators of Disease Progression in Polycystic Kidney Disease," Awarded May 1, 2017, downloaded Feb. 20, 2018, 2 pages.
NIH Grant 5R03DK099568-02, "Mirna-Based Therapeutics in Polycystic Kidney Disease," Awarded Jun. 14, 2014, downloaded Feb. 20, 2018, 2 pages.
Noureddine, et al., "MicroRNAs and Polycystic Kidney Disease," Drug Discovery Today, Disease Models, 2013, 10(3):e137-e143.
Office Action issued in Japanese Application No. 2018-510089, dated Jul. 2, 2020, and English language translation thereof.

(Continued)

*Primary Examiner* — Tracy Vivlemore

(74) *Attorney, Agent, or Firm* — Parker Highlander PLLC

(57) ABSTRACT

Provided herein are methods for the treatment of polycystic kidney disease, including autosomal dominant polycystic kidney disease, using modified oligonucleotides targeted to miR-17.

15 Claims, 2 Drawing Sheets

Specification includes a Sequence Listing.

(56) References Cited

OTHER PUBLICATIONS

Office Action issued in Russian Application No. 2018108206, dated Jan. 14, 2020, and English language translation thereof.
Patel et al, "miR-17~92 miRNA Cluster Promotes Kidney Cyst Growth in Polycystic Kidney Disease," PNAS, 2013, 110(26):10765-10770.
Patel et al., "Inactivation of miR-17~92 Suppresses Cyst Growth in Genetic Models of ADPKD," Presentation, Kidney Week, Oct. 2014, 17 pages.
Serva et al., "miR-17-5p Regulates Endocytic Trafficking Through Targeting TBC1D2/Armus," PLOS One, 2012, 7(12): e52555, 1-15.
Sun et al, "MicroRNA-17 Post-Transcriptionally Regulates Polycystic Kidney Disease-2 Gene and Promotes Cell Proliferation," Mol Biol Rep, 2010, 37(6):2951-2958.
Tran et al., "The RNA-Binding Protein Bicaudal C Regulates Polycystin 2 in the Kidney by Antagonizing miR-17 Activity," Development, 2010, 137(7):1107-1116.
Yheskel et al., "Therapeutic microRNAs in Polycystic Kidney Disease," Current Opin Nephrol Hypertens, 2017, 26: 1-8.

FIG. 1A

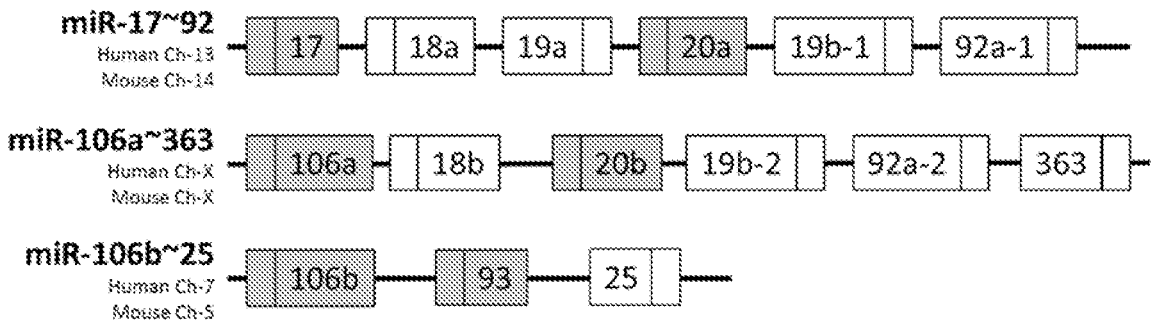

FIG. 1B

| miR-17 family | SEQUENCE (5' to 3')<br>Seed in bold | SEQ ID NO: |
|---|---|---|
| miR-17 | 5'-CAAAGUGCUUACAGUGCAGGUAG-3' | 1 |
| miR-20a | 5'-UAAAGUGCUUAUAGUGCAGGUAG-3' | 21 |
| miR-20b | 5'-CAAAGUGCUCAUAGUGCAGGUAG-3' | 22 |
| miR-93 | 5'-CAAAGUGCUCUUCGUGCAGGUAG-3' | 23 |
| miR-106a | 5'-AAAAGUGCUUACAGUGCAGGUAG-3' | 24 |
| miR-106b | 5'-UAAAGUGCUGACAGUGCAGAU-3' | 25 |
| miR-18 family | | |
| miR-18a | 5'-UAAGGUGCAUCUAGUGCAGAUAG-3' | 26 |
| miR-18b | 5'-UAAGGUGCAUCUAGUGCAGUUAG-3' | 27 |
| miR-19 family | | |
| miR-19a | 5'-UGUGCAAAUCUAUGCAAAACUGA-3' | 28 |
| miR-19b | 5'-UGUGCAAAUCCAUGCAAAACUGA-3' | 29 |
| miR-92 family | | |
| miR-25 | 5'-CAUUGCACUUGUCUCGGUCUGA-3' | 30 |
| miR-92a | 5'-UAUUGCACUUGUCCCGGCCUGU-3' | 31 |
| miR-363 | 5'-AAUUGCACGGUAUCCAUCUGUA-3' | 32 |

METHODS FOR TREATMENT OF POLYCYSTIC KIDNEY DISEASE

This application is a continuation of U.S. application Ser. No. 15/753,865, filed Feb. 20, 2018, which is a national stage application of International Application No. PCT/US2016/048603, filed Aug. 25, 2016, which claims the benefit of priority of U.S. Provisional Application No. 62/210,031, filed Aug. 26, 2015, each of which is incorporated by reference herein in its entirety for any purpose.

The sequence listing that is contained in the file named "RGLSP0002USC1.txt", which is 8 KB (as measured in Microsoft Windows®) and was created on Mar. 18, 2020, is filed herewith by electronic submission and is incorporated by reference herein.

FIELD OF INVENTION

Provided herein are methods and compositions for the treatment of polycystic kidney disease.

BACKGROUND

Polycystic kidney disease is a genetic disorder in which multiple fluid-filled cysts develop in the kidneys, and elsewhere in the body. Polycystic kidney disease can be inherited as autosomal recessive (ARPKD) or autosomal dominant (ADPKD). Autosomal dominant polycystic kidney disease is caused by mutations in the PKD1 or PKD2 gene. ADPKD is a progressive disease in which cyst formation and renal enlargement lead to renal insufficiency and eventually end-stage renal disease in 50% of patients by age 60. ADPKD patients may require lifelong dialysis and/or kidney transplant. There is currently no approved therapeutic agent for treating ADPKD.

SUMMARY OF INVENTION

Provided here are methods for treating polycystic kidney disease comprising administering to a subject in need thereof a therapeutically effective amount of a compound comprising a modified oligonucleotide consisting of 8 to 25 linked nucleosides, wherein the nucleobase sequence of the modified oligonucleotide is complementary to miR-17. In certain embodiments, the subject has polycystic kidney disease. In certain embodiments, the subject is suspected of having polycystic kidney disease.

In certain embodiments, the subject has been diagnosed as having polycystic kidney disease prior to administering the compound comprising the modified oligonucleotide. In some embodiments, the subject, prior to administration of the compound comprising the modified oligonucleotide, was determined to have an increased level of miR-17 in the kidney, urine or blood of the subject.

In certain embodiments, the polycystic kidney disease is autosomal dominant polycystic kidney disease (ADPKD). In some embodiments, the polycystic kidney disease is autosomal recessive polycystic kidney disease (ARPKD). In some embodiments, the subject has a mutation in the PKD1 gene. In some embodiments, the subject has a mutation in the PKD2 gene.

In certain embodiments, the subject has increased total kidney volume. In some embodiments, the subject has hypertension. In some embodiments, the subject has impaired kidney function. In some embodiments, the subject is in need of improved kidney function.

In any of the embodiments provided herein, administration of a compound comprising a modified oligonucleotide complementary to miR-17, to a subject having polycystic kidney disease, may improve kidney function in the subject; delay the worsening of kidney function in the subject; reduce total kidney volume in the subject; slow the increase in total kidney volume in the subject; inhibit cyst growth in the subject; slow the increase in cyst growth in the subject; reduce kidney pain in the subject; slow the increase in kidney pain in the subject; delay the onset of kidney pain in the subject; reduce hypertension in the subject; slow the worsening of hypertension in the subject; delay the onset of hypertension in the subject; reduce fibrosis in the kidney of the subject; slow the worsening of fibrosis in the kidney of the subject; delay the onset of end stage renal disease in the subject; delay time to dialysis for the subject; delay time to renal transplant for the subject; and/or improve life expectancy of the subject.

In any of the embodiments provided herein, administration of a compound comprising a modified oligonucleotide complementary to miR-17, to a subject having polycystic kidney disease, may reduce albuminuria in the subject; slow the worsening of albuminuria in the subject; delay the onset of albuminuria in the subject; reduce hematuria in the subject; slow the worsening of hematuria in the subject; delay the onset of hematuria in the subject; reduces blood urea nitrogen in the subject; reduce creatinine in the blood of the subject; improve creatinine clearance in the subject; reduce albumin:creatinine ratio in the subject; improve glomerular filtration rate in the subject; slows the worsening of glomerular filtration rate in the subject; reduce neutrophil gelatinase-associated lipocalin (NGAL) protein in the urine of the subject; and/or reduce kidney injury molecule-1 (KIM-1) protein in the urine of the subject.

Any of the embodiments provided herein may comprise measuring total kidney volume in the subject; measuring hypertension in the subject; measuring kidney pain in the subject; measuring fibrosis in the kidney of the subject; measuring blood urea nitrogen in the blood of the subject; measuring creatinine in the blood of the subject; measuring creatinine clearance in the subject; measuring albuminuria in the subject; measuring albumin:creatinine ratio in the subject; measuring glomerular filtration rate in the subject; measuring neutrophil gelatinase-associated lipocalin (NGAL) protein in the urine of the subject; and/or measuring kidney injury molecule-1 (KIM-1) protein in the urine of the subject.

In certain embodiments, the total kidney volume is height-adjusted kidney volume.

In certain embodiments, a cyst is present in the kidney of a subject. In some embodiments, a cyst is present in the kidney and liver of a subject.

Any of the embodiments provided herein may comprise administering at least one additional therapy that is an anti-hypertensive agent.

Any of the embodiments provided herein may comprise administering at least one additional therapy selected from an angiotensin II converting enzyme (ACE) inhibitor, an angiotensin II receptor blocker (ARB), a diuretic, a calcium channel blocker, a kinase inhibitor, an adrenergic receptor antagonist, a vasodilator, a benzodiazepine, a renin inhibitor, an aldosterone receptor antagonist, an endothelin receptor blocker, an mammalian target of rapamycin (mTOR) inhibitor, a hormone analogue, a vasopressin receptor 2 antagonist, an aldosterone receptor antagonist, dialysis, and kidney transplant.

In certain embodiments, a vasopressin receptor 2 antagonist is tolvaptan.

In certain embodiments, the angiotensin II converting enzyme (ACE) inhibitors is selected from captopril, enalapril, lisinopril, benazepril, quinapril, fosinopril, ramipril, cilazapril, perindopril, and trandolapril.

In certain embodiments, the angiotensin II receptor blockers (ARB) is selected from candesartan, irbesartan, olmesartan, losartan, valsartan, telmisartan, and eprosartan.

In certain embodiments, an ACE inhibitor is administered at a dose ranging from 0.5 to 1 mg/m²/day, from 1 to 6 mg/m²/day, from 1 to 2 mg/m²/day, from 2 to 4 mg/m²/day, or from 4 to 8 mg/m²/day.

In certain embodiments, an ARB is administered at a dose ranging from 6.25 to 150 mg/m2/day. In any of these embodiments, an ARB is administered at a dose of 6.25 mg/m²/day, 10 mg/m²/day, 12.5 mg/m²/day, 18.75 mg/m²/day, 37.5 mg/m²/day, 50 mg/m²/day, or 150 mg/m²/day.

In certain embodiments, the at least one additional therapy is an aldosterone receptor antagonist. In certain embodiments, an aldosterone receptor antagonist is spironolactone. In certain embodiments, spironolactone is administered at a dose ranging from 10 to 35 mg daily. In certain embodiments, spironolactone is administered at a dose of 25 mg daily.

In certain embodiments, a kinase inhibitor is selected from bosutinib and KD019.

In certain embodiments, an mTOR inhibitor is selected from everolimus, rapamycin, and sirolimus.

In certain embodiments, a hormone analogue is selected from somatostatin and adrenocorticotrophic hormone.

In any of the embodiments provided herein, the nucleobase sequence of the modified oligonucleotide is at least 90% complementary, is at least 95% complementary, or is 100% complementary to the nucleobase sequence of miR-17 (SEQ ID NO: 1).

In any of the embodiments provided herein, the nucleobase sequence of the modified oligonucleotide comprises the nucleobase sequence 5'-GCACTTTG-3' (SEQ ID NO: 3), wherein each T in the nucleobase sequence is independently selected from a T and a U.

In any of the embodiments provided herein, the modified oligonucleotide consists of 8 to 25, 8 to 12, 12 to 25, 15 to 25, or 17 to 23 linked nucleosides. In any of the embodiments provided herein, the modified oligonucleotide consists of 8, 9, 10, 11 or 12 linked nucleosides. In any of the embodiments provided herein, the modified oligonucleotide consists of 12, 13, 14, 15, 16, 17, 18, 19, 20, 21, 22, 23, 24, or 25 linked nucleosides. In any of the embodiments provided herein, the modified oligonucleotide consists of 15, 16, 17, 18, 19, 20, 21, 22, 23, 24, or 25 linked nucleosides. In any of the embodiments provided herein, the modified oligonucleotide consists of 17, 18, 19, 20, 21, 22, or 23 linked nucleosides.

In any of the embodiments provided herein, the modified oligonucleotide comprises at least one modified nucleoside. The modified nucleoside may be selected from an S-cEt nucleoside, a 2'-O-methoxyethyl nucleoside, and an LNA nucleoside. The modified oligonucleotide may comprise at least one modified internucleoside linkage. Each internucleoside linkage of the modified oligonucleotide may be a modified internucleoside linkage. In certain embodiments, the modified internucleoside linkage is a phosphorothioate internucleoside linkage.

In any of the embodiments provided herein, the compound consists of the modified oligonucleotide.

In any of the embodiments provided herein, a therapeutically effective amount of the compound comprising a modified oligonucleotide complementary to miR-17 is administered to the subject.

Provided herein is the use of a compound comprising a modified oligonucleotide consisting of 8 to 25 linked nucleosides, wherein the nucleobase sequence of the modified oligonucleotide is complementary to miR-17, for the treatment of polycystic kidney disease.

BRIEF DESCRIPTION OF FIGURES

FIG. 1A-B. (A) Genomic organization of the miR-17~92 and its paralogous clusters miR-106a~363 and miR-106b~25; (B) miR-17, miR-18, miR-19, and miR-92 microRNA families.

DETAILED DESCRIPTION

Figure 2A:
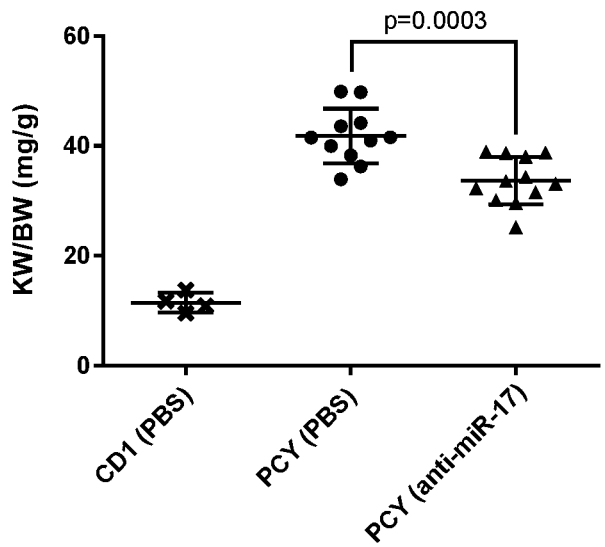
FIG. 2A-B. Treatment of Pcy mice with anti-miR-17 leads to (A) reduction in kidney weight to body weight ratio and (B) cystic index.

Unless defined otherwise, all technical and scientific terms used herein have the same meaning as is commonly understood by one of skill in the arts to which the invention belongs. Unless specific definitions are provided, the nomenclature utilized in connection with, and the procedures and techniques of, analytical chemistry, synthetic organic chemistry, and medicinal and pharmaceutical chemistry described herein are those well-known and commonly used in the art. In the event that there is a plurality of definitions for terms herein, those in this section prevail. Standard techniques may be used for chemical synthesis, chemical analysis, pharmaceutical preparation, formulation and delivery, and treatment of subjects. Certain such techniques and procedures may be found for example in "Carbohydrate Modifications in Antisense Research" Edited by Sangvi and Cook, American Chemical Society, Washington D.C., 1994; and "Remington's Pharmaceutical Sciences," Mack Publishing Co., Easton, Pa., 18th edition, 1990; and which is hereby incorporated by reference for any purpose. Where permitted, all patents, patent applications, published applications and publications, GENBANK sequences, websites and other published materials referred to throughout the entire disclosure herein, unless noted otherwise, are incorporated by reference in their entirety. Where reference is made to a URL or other such identifier or address, it is understood that such identifiers can change and particular information on the internet can change, but equivalent information can be found by searching the internet. Reference thereto evidences the availability and public dissemination of such information.

Before the present compositions and methods are disclosed and described, it is to be understood that the terminology used herein is for the purpose of describing particular embodiments only and is not intended to be limiting. It must be noted that, as used in the specification and the appended claims, the singular forms "a," "an" and "the" include plural referents unless the context clearly dictates otherwise.

Definitions

"Polycystic kidney disease" or "PKD" is an inherited form of kidney disease in which multiple cysts form in at least one kidney, leading to enlargement of the affected kidney(s) and progressive loss of kidney function.

"Autosomal dominant polycystic kidney disease" or "ADPKD" is typically caused by one or more genetic mutations in the PKD1 and/or PKD2 gene. 85% of ADPKD is caused by mutations in PKD1, which is located on chromosome 16, with the majority of the remaining ADPKD cases caused by mutations in PKD2, which is located on chromosome 4.

"Autosomal recessive polycystic kidney disease" or "ARPKD" is typically caused by one or more genetic mutations in the PKHD1 gene, which is located on chromosome 6. Up to 50% of neonates with ARPKD die from complications of intrauterine kidney disease, and about a third of those who survive develop end stage renal disease (ESRD) within 10 years.

"Total kidney volume" or "TKV" is a measurement of total kidney volume which may be determined by Magnetic Resonance Imaging (MRI), Computed Tomography (CT) scan, or ultrasound (US) imaging, and the volume calculated by a standard methodology, such as an ellipsoid volume equation (for ultrasound), or by quantitative stereology or boundary tracing (for CT/MRI). TKV generally increases steadily in ADPKD patients, with increases correlating with a decline in kidney function.

"Height-adjusted total kidney volume" or "HtTKV" is a measure of total kidney volume per unit height. Patients with an HtTKV value≥600 ml/m are predicted to develop stage 3 chronic kidney disease within 8 years.

"Kidney pain" means clinically significant kidney pain necessitating medical leave, pharmacologic treatment (narcotic or last-resort analgesic agents), or invasive intervention.

"Worsening hypertension" means a change in blood pressure that requires an increase in hypertensive treatment.

"Fibrosis" means the formation or development of excess fibrous connective tissue in an organ or tissue. In certain embodiments, fibrosis occurs as a reparative or reactive process. In certain embodiments, fibrosis occurs in response to damage or injury. The term "fibrosis" is to be understood as the formation or development of excess fibrous connective tissue in an organ or tissue as a reparative or reactive process, as opposed to a formation of fibrous tissue as a normal constituent of an organ or tissue.

"Hematuria" means the presence of red blood cells in the urine.

"Albuminuria" means the presence of excess albumin in the urine, and includes without limitation, normal albuminuria, high normal albuminuria, microalbuminuria and macroalbuminuria. Normally, the glomerular filtration permeability barrier, which is composed of podocyte, glomerular basement membrane and endothelial cells, prevents serum protein from leaking into urine. Albuminuria may reflect injury of the glomerular filtration permeability barrier. Albuminuria may be calculated from a 24-hour urine sample, an overnight urine sample or a spot-urine sample.

"High normal albuminuria" means elevated albuminuria characterized by (i) the excretion of 15 to <30 mg of albumin into the urine per 24 hours and/or (ii) an albumin/creatinine ratio of 1.25 to <2.5 mg/mmol (or 10 to <20 mg/g) in males or 1.75 to <3.5 mg/mmol (or 15 to <30 mg/g) in females.

"Microalbuminuria" means elevated albuminuria characterized by (i) the excretion of 30 to 300 mg of albumin into the urine per 24 hours and/or (ii) an albumin/creatinine ratio of 2.5 to <25 mg/mmol (or 20 to <200 mg/g) in males or 3.5 to <35 mg/mmol (or 30 to <300 mg/g) in females.

"Macroalbuminuria" means elevated albuminuria characterized by the excretion of more than 300 mg of albumin into the urine per 24 hours and/or (ii) an albumin/creatinine ratio of >25 mg/mmol (or >200 mg/g) in males or >35 mg/mmol (or >300 mg/g) in females.

"Albumin/creatinine ratio" means the ratio of urine albumin (mg/dL) per urine creatinine (g/dL) and is expressed as mg/g. In certain embodiments, albumin/creatinine ratio may be calculated from a spot-urine sample and may be used as an estimate of albumin excretion over a 24 hour period.

"Estimated glomerular filtration rate (eGFR) or "glomerular filtration rate (GFR)" means a measurement of how well the kidneys are filtering creatinine, and is used as an estimate of how much blood passes through the glomeruli per minute. Normal results may range from 90-120 mL/min/1.73 m$^2$. Levels below 60 mL/min/1.73 m$^2$ for 3 or more months may be an indicator chronic kidney disease. Levels below 15 mL/min/1.73 m$^2$ may be an indicator of kidney failure.

"Proteinuria" means the presence of an excess of serum proteins in the urine. Proteinuria may be characterized by the excretion of >250 mg of protein into the urine per 24 hours and/or a urine protein to creatinine ratio of ≥0.20 mg/mg. Serum proteins elevated in association with proteinuria include, without limitation, albumin.

"Blood urea nitrogen" or "BUN" means a measure of the amount of nitrogen in the blood in the form of urea. The liver produces urea in the urea cycle as a waste product of the digestion of protein, and the urea is removed from the blood by the kidneys. Normal human adult blood may contain between 7 to 21 mg of urea nitrogen per 100 ml (7-21 mg/dL) of blood. Measurement of blood urea nitrogen is used as an indicator of renal health. If the kidneys are not able to remove urea from the blood normally, a subject's BUN rises.

"End stage renal disease (ESRD)" means the complete or almost complete failure of kidney function.

"Impaired kidney function" means reduced kidney function, relative to normal kidney function.

"Slow the worsening of" and "slow worsening" mean to reduce the rate at which a medical condition moves towards an advanced state.

"Delay time to dialysis" means to maintain sufficient kidney function such that the need for dialysis treatment is delayed.

"Delay time to renal transplant" means to maintain sufficient kidney function such that the need for a kidney transplant is delayed.

"Improves life expectancy" means to lengthen the life of a subject by treating one or more symptoms of a disease in the subject.

"Subject" means a human or non-human animal selected for treatment or therapy.

"Subject in need thereof" means a subject that is identified as in need of a therapy or treatment.

"Subject suspected of having" means a subject exhibiting one or more clinical indicators of a disease.

"Administering" means providing a pharmaceutical agent or composition to a subject, and includes, but is not limited to, administering by a medical professional and self-administering.

"Parenteral administration" means administration through injection or infusion. Parenteral administration includes, but is not limited to, subcutaneous administration, intravenous administration, and intramuscular administration.

"Subcutaneous administration" means administration just below the skin.

"Intravenous administration" means administration into a vein.

"Administered concomitantly" refers to the co-administration of two or more agents in any manner in which the pharmacological effects of both are manifest in the patient at the same time. Concomitant administration does not require that both agents be administered in a single pharmaceutical composition, in the same dosage form, or by the same route of administration. The effects of both agents need not manifest themselves at the same time. The effects need only be overlapping for a period of time and need not be coextensive.

"Duration" means the period of time during which an activity or event continues. In certain embodiments, the duration of treatment is the period of time during which doses of a pharmaceutical agent or pharmaceutical composition are administered.

"Therapy" means a disease treatment method. In certain embodiments, therapy includes, but is not limited to, administration of one or more pharmaceutical agents to a subject having a disease.

"Treat" means to apply one or more specific procedures used for the cure of a disease or the amelioration at least one indicator of a disease. In certain embodiments, the specific procedure is the administration of one or more pharmaceutical agents. In certain embodiments, treatment of PKD includes, but is not limited to, reducing total kidney volume, improving kidney function, reducing hypertension, and/or reducing kidney pain.

"Ameliorate" means to lessen the severity of at least one indicator of a condition or disease. In certain embodiments, amelioration includes a delay or slowing in the progression of one or more indicators of a condition or disease. The severity of indicators may be determined by subjective or objective measures which are known to those skilled in the art.

"At risk for developing" means the state in which a subject is predisposed to developing a condition or disease. In certain embodiments, a subject at risk for developing a condition or disease exhibits one or more symptoms of the condition or disease, but does not exhibit a sufficient number of symptoms to be diagnosed with the condition or disease. In certain embodiments, a subject at risk for developing a condition or disease exhibits one or more symptoms of the condition or disease, but to a lesser extent required to be diagnosed with the condition or disease.

"Prevent the onset of" means to prevent the development of a condition or disease in a subject who is at risk for developing the disease or condition. In certain embodiments, a subject at risk for developing the disease or condition receives treatment similar to the treatment received by a subject who already has the disease or condition.

"Delay the onset of" means to delay the development of a condition or disease in a subject who is at risk for developing the disease or condition. In certain embodiments, a subject at risk for developing the disease or condition receives treatment similar to the treatment received by a subject who already has the disease or condition.

"Therapeutic agent" means a pharmaceutical agent used for the cure, amelioration or prevention of a disease.

"Dose" means a specified quantity of a pharmaceutical agent provided in a single administration. In certain embodiments, a dose may be administered in two or more boluses, tablets, or injections. For example, in certain embodiments, where subcutaneous administration is desired, the desired dose requires a volume not easily accommodated by a single injection. In such embodiments, two or more injections may be used to achieve the desired dose. In certain embodiments, a dose may be administered in two or more injections to minimize injection site reaction in an individual. In certain embodiments, a dose is administered as a slow infusion.

"Dosage unit" means a form in which a pharmaceutical agent is provided. In certain embodiments, a dosage unit is a vial containing lyophilized oligonucleotide. In certain embodiments, a dosage unit is a vial containing reconstituted oligonucleotide.

"Therapeutically effective amount" refers to an amount of a pharmaceutical agent that provides a therapeutic benefit to an animal.

"Pharmaceutical composition" means a mixture of substances suitable for administering to an individual that includes a pharmaceutical agent. For example, a pharmaceutical composition may comprise a sterile aqueous solution.

"Pharmaceutical agent" means a substance that provides a therapeutic effect when administered to a subject.

"Active pharmaceutical ingredient" means the substance in a pharmaceutical composition that provides a desired effect.

"Pharmaceutically acceptable salt" means a physiologically and pharmaceutically acceptable salt of a compound provided herein, i.e., a salt that retains the desired biological activity of the compound and does not have undesired toxicological effects when administered to a subject. Non-limiting exemplary pharmaceutically acceptable salts of compounds provided herein include sodium and potassium salt forms. The term "compound" as used herein includes pharmaceutically acceptable salts thereof unless specifically indicated otherwise.

"Improved organ function" means a change in organ function toward normal limits. In certain embodiments, organ function is assessed by measuring molecules found in a subject's blood or urine. For example, in certain embodiments, improved kidney function is measured by a reduction in blood urea nitrogen, a reduction in proteinuria, a reduction in albuminuria, etc.

"Acceptable safety profile" means a pattern of side effects that is within clinically acceptable limits.

"Side effect" means a physiological response attributable to a treatment other than desired effects. In certain embodiments, side effects include, without limitation, injection site reactions, liver function test abnormalities, kidney function abnormalities, liver toxicity, renal toxicity, central nervous system abnormalities, and myopathies. Such side effects may be detected directly or indirectly. For example, increased aminotransferase levels in serum may indicate liver toxicity or liver function abnormality. For example, increased bilirubin may indicate liver toxicity or liver function abnormality.

"Subject compliance" means adherence to a recommended or prescribed therapy by a subject.

"Comply" means the adherence with a recommended therapy by a subject.

"Recommended therapy" means a treatment recommended by a medical professional for the treatment, amelioration, or prevention of a disease.

The term "blood" as used herein, encompasses whole blood and blood fractions, such as serum and plasma.

"Anti-miR" means an oligonucleotide having a nucleobase sequence complementary to a microRNA. In certain embodiments, an anti-miR is a modified oligonucleotide.

"Anti-miR-X" where "miR-X" designates a particular microRNA, means an oligonucleotide having a nucleobase sequence complementary to miR-X. In certain embodiments, an anti-miR-X is fully complementary (i.e., 100% complementary) to miR-X. In certain embodiments, an anti-miR-X is at least 80%, at least 85%, at least 90%, or at least 95% complementary to miR-X. In certain embodiments, an anti-miR-X is a modified oligonucleotide.

"miR-17" means the mature miRNA having the nucleobase sequence

CAAAGUGCUUACAGUGCAGGUAG. (SEQ ID NO: 1)

"miR-17 stem-loop sequence" means the stem-loop sequence having the nucleobase sequence GUCAGAAUAAUGUCAAAGUGCUUACAGUGCAGGUAGUGAUAUGUGCAUCUA (SEQ ID NO: 2)
CUGCAGUGAAGGCACUUGUAGCAUUAUGGUGAC.

"miR-17 2-7 seed sequence" means the nucleobase sequence from positions 2 to 7 of SEQ ID NO: 1, AAAGUG.

"miR-17 family member" means a mature miRNA having a nucleobase sequence comprising the miR-17 2-7 seed sequence.

"miR-17 family" means a group of miRNAs, each having a nucleobase sequence comprising the miR-17 2-7 seed sequence.

"Target nucleic acid" means a nucleic acid to which an oligomeric compound is designed to hybridize.

"Targeting" means the process of design and selection of nucleobase sequence that will hybridize to a target nucleic acid.

"Targeted to" means having a nucleobase sequence that will allow hybridization to a target nucleic acid.

"Modulation" means a perturbation of function, amount, or activity. In certain embodiments, modulation means an increase in function, amount, or activity. In certain embodiments, modulation means a decrease in function, amount, or activity.

"Expression" means any functions and steps by which a gene's coded information is converted into structures present and operating in a cell.

"Nucleobase sequence" means the order of contiguous nucleobases in an oligomeric compound or nucleic acid, typically listed in a 5' to 3' orientation, independent of any sugar, linkage, and/or nucleobase modification.

"Contiguous nucleobases" means nucleobases immediately adjacent to each other in a nucleic acid.

"Nucleobase complementarity" means the ability of two nucleobases to pair non-covalently via hydrogen bonding.

"Complementary" means that one nucleic acid is capable of hybridizing to another nucleic acid or oligonucleotide. In certain embodiments, complementary refers to an oligonucleotide capable of hybridizing to a target nucleic acid.

"Fully complementary" means each nucleobase of an oligonucleotide is capable of pairing with a nucleobase at each corresponding position in a target nucleic acid. In certain embodiments, an oligonucleotide is fully complementary to a microRNA, i.e. each nucleobase of the oligonucleotide is complementary to a nucleobase at a corresponding position in the microRNA. A modified oligonucleotide may be fully complementary to a microRNA, and have a number of linked nucleosides that is less than the length of the microRNA. For example, an oligonucleotide with 16 linked nucleosides, where each nucleobase of the oligonucleotide is complementary to a nucleobase at a corresponding position in a microRNA, is fully complementary to the microRNA. In certain embodiments, an oligonucleotide wherein each nucleobase has complementarity to a nucleobase within a region of a microRNA stem-loop sequence is fully complementary to the microRNA stem-loop sequence.

"Percent complementarity" means the percentage of nucleobases of an oligonucleotide that are complementary to an equal-length portion of a target nucleic acid. Percent complementarity is calculated by dividing the number of nucleobases of the oligonucleotide that are complementary to nucleobases at corresponding positions in the target nucleic acid by the total number of nucleobases in the oligonucleotide.

"Percent identity" means the number of nucleobases in a first nucleic acid that are identical to nucleobases at corresponding positions in a second nucleic acid, divided by the total number of nucleobases in the first nucleic acid. In certain embodiments, the first nucleic acid is a microRNA and the second nucleic acid is a microRNA. In certain embodiments, the first nucleic acid is an oligonucleotide and the second nucleic acid is an oligonucleotide.

"Hybridize" means the annealing of complementary nucleic acids that occurs through nucleobase complementarity.

"Mismatch" means a nucleobase of a first nucleic acid that is not capable of Watson-Crick pairing with a nucleobase at a corresponding position of a second nucleic acid.

"Identical" in the context of nucleobase sequences, means having the same nucleobase sequence, independent of sugar, linkage, and/or nucleobase modifications and independent of the methyl state of any pyrimidines present.

"MicroRNA" means an endogenous non-coding RNA between 18 and 25 nucleobases in length, which is the product of cleavage of a pre-microRNA by the enzyme Dicer. Examples of mature microRNAs are found in the microRNA database known as miRBase (http://microrna.sanger.ac.uk/). In certain embodiments, microRNA is abbreviated as "microRNA" or "miR."

"Pre-microRNA" or "pre-miR" means a non-coding RNA having a hairpin structure, which is the product of cleavage of a pri-miR by the double-stranded RNA-specific ribonuclease known as Drosha.

"Stem-loop sequence" means an RNA having a hairpin structure and containing a mature microRNA sequence. Pre-microRNA sequences and stem-loop sequences may overlap. Examples of stem-loop sequences are found in the microRNA database known as miRBase (http://microrna.sanger.ac.uk/).

"Pri-microRNA" or "pri-miR" means a non-coding RNA having a hairpin structure that is a substrate for the double-stranded RNA-specific ribonuclease Drosha.

"microRNA precursor" means a transcript that originates from a genomic DNA and that comprises a non-coding, structured RNA comprising one or more microRNA sequences. For example, in certain embodiments a microRNA precursor is a pre-microRNA. In certain embodiments, a microRNA precursor is a pri-microRNA.

"microRNA-regulated transcript" means a transcript that is regulated by a microRNA.

"Seed sequence" means a nucleobase sequence comprising from 6 to 8 contiguous nucleobases of nucleobases 1 to 9 of the 5'-end of a mature microRNA sequence.

"Seed match sequence" means a nucleobase sequence that is complementary to a seed sequence, and is the same length as the seed sequence.

"Oligomeric compound" means a compound that comprises a plurality of linked monomeric subunits. Oligomeric compounds include oligonucleotides.

"Oligonucleotide" means a compound comprising a plurality of linked nucleosides, each of which can be modified or unmodified, independent from one another.

"Naturally occurring internucleoside linkage" means a 3' to 5' phosphodiester linkage between nucleosides.

"Natural sugar" means a sugar found in DNA (2'-H) or RNA (2'-OH).

"Internucleoside linkage" means a covalent linkage between adjacent nucleosides.

"Linked nucleosides" means nucleosides joined by a covalent linkage.

"Nucleobase" means a heterocyclic moiety capable of non-covalently pairing with another nucleobase.

"Nucleoside" means a nucleobase linked to a sugar moiety.

"Nucleotide" means a nucleoside having a phosphate group covalently linked to the sugar portion of a nucleoside.

"Compound comprising a modified oligonucleotide consisting of" a number of linked nucleosides means a compound that includes a modified oligonucleotide having the specified number of linked nucleosides. Thus, the compound may include additional substituents or conjugates. Unless otherwise indicated, the compound does not include any additional nucleosides beyond those of the modified oligonucleotide. For example, unless otherwise indicated, a compound comprising a modified oligonucleotide does not include a complementary strand hybridized to the modified oligonucleotide (i.e., the modified oligonucleotide is a single-stranded modified oligonucleotide).

"Modified oligonucleotide" means an oligonucleotide having one or more modifications relative to a naturally occurring terminus, sugar, nucleobase, and/or internucleoside linkage. A modified oligonucleotide may comprise unmodified nucleosides.

"Single-stranded modified oligonucleotide" means a modified oligonucleotide which is not hybridized to a complementary strand.

"Modified nucleoside" means a nucleoside having any change from a naturally occurring nucleoside. A modified nucleoside may have a modified sugar and an unmodified nucleobase. A modified nucleoside may have a modified sugar and a modified nucleobase. A modified nucleoside may have a natural sugar and a modified nucleobase. In certain embodiments, a modified nucleoside is a bicyclic nucleoside. In certain embodiments, a modified nucleoside is a non-bicyclic nucleoside.

"Modified internucleoside linkage" means any change from a naturally occurring internucleoside linkage.

"Phosphorothioate internucleoside linkage" means a linkage between nucleosides where one of the non-bridging atoms is a sulfur atom.

"Modified sugar moiety" means substitution and/or any change from a natural sugar.

"Unmodified nucleobase" means the naturally occurring heterocyclic bases of RNA or DNA: the purine bases adenine (A) and guanine (G), and the pyrimidine bases thymine (T), cytosine (C) (including 5-methylcytosine), and uracil (U).

"5-methylcytosine" means a cytosine comprising a methyl group attached to the 5 position.

"Non-methylated cytosine" means a cytosine that does not have a methyl group attached to the 5 position.

"Modified nucleobase" means any nucleobase that is not an unmodified nucleobase.

"Sugar moiety" means a naturally occurring furanosyl or a modified sugar moiety.

"Modified sugar moiety" means a substituted sugar moiety or a sugar surrogate.

"2'-O-methyl sugar" or "2'-OMe sugar" means a sugar having an O-methyl modification at the 2' position.

"2'-O-methoxyethyl sugar" or "2'-MOE sugar" means a sugar having an O-methoxyethyl modification at the 2' position.

"2'-fluoro" or "2'-F" means a sugar having a fluoro modification of the 2' position.

"Bicyclic sugar moiety" means a modified sugar moiety comprising a 4 to 7 membered ring (including by not limited to a furanosyl) comprising a bridge connecting two atoms of the 4 to 7 membered ring to form a second ring, resulting in a bicyclic structure. In certain embodiments, the 4 to 7 membered ring is a sugar ring. In certain embodiments the 4 to 7 membered ring is a furanosyl. In certain such embodiments, the bridge connects the 2'-carbon and the 4'-carbon of the furanosyl. Nonlimiting exemplary bicyclic sugar moieties include LNA, ENA, cEt, S-cEt, and R-cEt.

"Locked nucleic acid (LNA) sugar moiety" means a substituted sugar moiety comprising a $(CH_2)$—O bridge between the 4' and 2' furanose ring atoms.

"ENA sugar moiety" means a substituted sugar moiety comprising a $(CH_2)_2$—O bridge between the 4' and 2' furanose ring atoms.

"Constrained ethyl (cEt) sugar moiety" means a substituted sugar moiety comprising a $CH(CH_3)$—O bridge between the 4' and the 2' furanose ring atoms. In certain embodiments, the $CH(CH_3)$—O bridge is constrained in the S orientation. In certain embodiments, the $(CH_2)_2$—O is constrained in the R orientation.

"S-cEt sugar moiety" means a substituted sugar moiety comprising an S-constrained $CH(CH_3)$—O bridge between the 4' and the 2' furanose ring atoms.

"R-cEt sugar moiety" means a substituted sugar moiety comprising an R-constrained $CH(CH_3)$—O bridge between the 4' and the 2' furanose ring atoms.

"2'-O-methyl nucleoside" means a 2'-modified nucleoside having a 2'-O-methyl sugar modification.

"2'-O-methoxyethyl nucleoside" means a 2'-modified nucleoside having a 2'-O-methoxyethyl sugar modification. A 2'-O-methoxyethyl nucleoside may comprise a modified or unmodified nucleobase.

"2'-fluoro nucleoside" means a 2'-modified nucleoside having a 2'-fluoro sugar modification. A 2'-fluoro nucleoside may comprise a modified or unmodified nucleobase.

"Bicyclic nucleoside" means a 2'-modified nucleoside having a bicyclic sugar moiety. A bicyclic nucleoside may have a modified or unmodified nucleobase.

"cEt nucleoside" means a nucleoside comprising a cEt sugar moiety. A cEt nucleoside may comprise a modified or unmodified nucleobase.

"S-cEt nucleoside" means a nucleoside comprising an S-cEt sugar moiety.

"R-cEt nucleoside" means a nucleoside comprising an R-cEt sugar moiety.

"β-D-deoxyribonucleoside" means a naturally occurring DNA nucleoside.

"β-D-ribonucleoside" means a naturally occurring RNA nucleoside.

"LNA nucleoside" means a nucleoside comprising a LNA sugar moiety.

"ENA nucleoside" means a nucleoside comprising an ENA sugar moiety.

Overview

Polycystic kidney disease (PKD) is an inherited form of kidney disease in which fluid-filled cysts develop in the kidneys, leading to kidney enlargement, renal insufficiency, and often end-stage renal disease. The excessive proliferation of cysts is a hallmark pathological feature of PKD. In the management of PKD, the primary goal for treatment is to maintain kidney function and prevent the onset of end-stage renal disease (ESRD), which in turn improves life expectancy of subjects with PKD.

Multiple members of the miR-17-92 cluster of microRNAs are upregulated in mouse models of PKD. Genetic deletion of the miR-17-92 cluster in a mouse model of PKD reduces kidney cyst growth, improves renal function, and prolongs survival (Patel et al., *PNAS*, 2013; 110(26): 10765-10770). The miR-17-92 cluster contains 6 different microRNAs, each with distinct sequences: miR-17, miR-18a, miR-19a, miR-19-b-1 and miR-92a-1. Thus, genetic deletion of the entire cluster deletes six different microRNA genes. What this genetic deletion experiment does not demonstrate is whether inhibition of a subset of microRNAs in the cluster would produce the same improvements in clinical markers of PKD.

It is demonstrated herein that a modified oligonucleotide targeted to miR-17 improves kidney function and reduces kidney weight in an experimental model of PKD. Further, miR-17 inhibition also suppressed proliferation and cyst growth of primary cultures derived from cysts of human donors. These data demonstrate that modified oligonucleotides targeted to miR-17 are useful for the treatment of PKD.

Certain Uses of the Invention

Provided herein are methods for the treatment of polycystic kidney disease (PKD), comprising administering to a subject having or suspected of having PKD a compound comprising a modified oligonucleotide complementary to miR-17.

In certain embodiments, the subject has been diagnosed as having PKD prior to administration of the compound comprising the modified oligonucleotide. Diagnosis of PKD may be achieved through evaluation of parameters including, without limitation, a subject's family history, clinical features (including without limitation hypertension, albuminuria, hematuria, and impaired GFR), and kidney imaging studies (including without limitation MRI, ultrasound, and CT scan). Diagnosis of PKD may also include screening for mutations in one or more of the PKD1, PKD2, or PKHD1 genes.

The subject having or suspected of having ADPKD may have a mutation in the PKD1 gene or a mutation in the PKD2 gene. The subject having or suspected of having ARPKD may have a mutation in the PKHD1 gene.

In certain embodiments the subject has an increased total kidney volume. In certain embodiments, the total kidney volume is height-adjusted total kidney volume (HtTKV). In certain embodiments, the subject has hypertension. In certain embodiments, the subject has impaired kidney function. In certain embodiments, the subject is in need of improved kidney function. In certain embodiments, the subject is identified as having impaired kidney function.

In certain embodiments, levels of miR-17 are increased in the kidney of a subject having PKD. In certain embodiments, prior to administration, a subject is determined to have an increased level of miR-17 in the kidney. miR-17 levels may be measured from kidney biopsy material. In certain embodiments, prior to administration, a subject is determined to have an increased level of miR-17 in the urine or blood of the subject.

In certain embodiments, administration of a compound comprising a modified oligonucleotide complementary to miR-17 results in one or more clinically beneficial outcomes. In certain embodiments the administration improves kidney function in the subject. In certain embodiments the administration delays the worsening of kidney function in the subject. In certain embodiments the administration reduces total kidney volume in the subject. In certain embodiments the administration slows the increase in total kidney volume in the subject. In certain embodiments, the administration reduces height-adjusted total kidney volume (HtTKV). In certain embodiments, the administration slows an increase in HtTKV.

In certain embodiments the administration inhibits cyst growth in the subject. In certain embodiments the administration slows the increase in cyst growth in the subject. In some embodiments, a cyst is present in the kidney of a subject. In some embodiments, a cyst is present in both the liver and the kidney of the subject.

In certain embodiments the administration reduces kidney pain in the subject. In certain embodiments the administration slows the increase in kidney pain in the subject. In certain embodiments the administration delays the onset of kidney pain in the subject.

In certain embodiments the administration reduces hypertension in the subject. In certain embodiments the administration slows the worsening of hypertension in the subject. In certain embodiments the administration delays the onset of hypertension in the subject.

In certain embodiments the administration reduces fibrosis in kidney of the subject. In certain embodiments the administration slows the fibrosis in the kidney of the subject.

In certain embodiments the administration delays the onset of end stage renal disease in the subject. In certain embodiments the administration delays time to dialysis for the subject. In certain embodiments the administration delays time to renal transplant for the subject. In certain embodiments the administration improves life expectancy of the subject.

In certain embodiments the administration reduces albuminuria in the subject. In certain embodiments the administration slows the worsening of albuminuria in the subject. In certain embodiments the administration delays the onset of albuminuria in the subject. In certain embodiments the administration reduces hematuria in the subject. In certain embodiments the administration slows the worsening of hematuria in the subject. In certain embodiments the administration delays the onset of hematuria in the subject. In certain embodiments the administration reduces blood urea nitrogen in the subject. In certain embodiments the administration reduces creatinine in the blood of the subject. In certain embodiments the administration improves creatinine clearance in the subject. In certain embodiments the administration reduces albumin:creatinine ratio in the subject. In certain embodiments the administration improves glomerular filtration rate in the subject. In certain embodiments, the administration slows the worsening of glomerular filtration rate in the subject. In some embodiments, the worsening of glomerular filtration rate is assessed by calculating the rate of decline of glomerular filtration rate. In certain embodiments the administration reduces neutrophil gelatinase-associated lipocalin (NGAL) protein in the urine of the subject. In certain embodiments the administration reduces kidney injury molecule-1 (KIM-1) protein in the urine of the subject.

In any of the embodiments provided herein, a subject may be subjected to certain tests to evaluate the extent of disease in the subject. Such tests include, without limitation, measurement of total kidney volume in the subject; measurement of hypertension in the subject; measurement of kidney pain in the subject; measurement of fibrosis in the kidney of the subject; measurement of blood urea nitrogen in the subject; measuring creatinine in the blood of the subject; measuring creatinine clearance in the blood of the subject; measuring albuminuria in the subject; measuring albumin:creatinine ratio in the subject; measuring glomerular filtration rate in the subject; measurement of neutrophil gelatinase-associated lipocalin (NGAL) protein in the urine of the subject; and/or measurement of kidney injury molecule-1 (KIM-1) protein in the urine of the subject Certain Additional Therapies Treatments for polycystic kidney disease or any of the conditions listed herein may comprise more than one therapy. As such, in certain embodiments provided herein are methods for treating a subject having or suspected of having polycystic kidney disease comprising administering at least one therapy in addition to administering compound comprising a modified oligonucleotide having a nucleobase sequence complementary to a miR-17.

In certain embodiments, the at least one additional therapy comprises a pharmaceutical agent.

In certain embodiments, the at least one additional therapy is an anti-hypertensive agent. Anti-hypertensive agents are used to control blood pressure of the subject.

In certain embodiments, a pharmaceutical agent is a vasopressin receptor 2 antagonist. In certain embodiments, a vasopressin receptor 2 antagonist is tolvaptan.

In certain embodiments, pharmaceutical agents include angiotensin II receptor blockers (ARB). In certain embodiments, an angiotensin II receptor blocker is candesartan, irbesartan, olmesartan, losartan, valsartan, telmisartan, or eprosartan. In certain embodiments, an ARB is administered at a dose ranging from 6.25 to 150 mg/m2/day. In any of these embodiments, an ARB is administered at a dose of 6.25 mg/m$^2$/day, 10 mg/m$^2$/day, 12.5 mg/m$^2$/day, 18.75 mg/m$^2$/day, 37.5 mg/m$^2$/day, 50 mg/m$^2$/day, or 150 mg/m$^2$/day.

In certain embodiments, pharmaceutical agents include angiotensin II converting enzyme (ACE) inhibitors. In certain embodiments, an ACE inhibitor is captopril, enalapril, lisinopril, benazepril, quinapril, fosinopril, or ramipril. In certain embodiments, an ACE inhibitor is administered at a dose ranging from 0.5 to 1 mg/m2/day, from 1 to 6 mg/m2/day, from 1 to 2 mg/m2/day, from 2 to 4 mg/m2/day, or from 4 to 8 mg/m2/day.

In certain embodiments, a pharmaceutical agents is a diuretic. In certain embodiments, a pharmaceutical agent is a calcium channel blocker.

In certain embodiments, a pharmaceutical agent is a kinase inhibitor. In certain embodiments, a kinase inhibitor is bosutinib or KD019.

In certain embodiments, a pharmaceutical agent is an adrenergic receptor antagonist.

In certain embodiments, a pharmaceutical agent is an aldosterone receptor antagonist. In certain embodiments, an aldosterone receptor antagonist is spironolactone. In certain embodiments, spironolactone is administered at a dose ranging from 10 to 35 mg daily. In certain embodiments, spironolactone is administered at a dose of 25 mg daily.

In certain embodiments, a pharmaceutical agent is a mammalian target of rapamycin (mTOR) inhibitor. In certain embodiments, an mTOR inhibitor is everolimus, rapamycin, or sirolimus.

In certain embodiments, a pharmaceutical agent is a hormone analogue. In certain embodiments, a hormone analogue is somatostatin or adrenocorticotrophic hormone.

In certain embodiments, an additional therapy is an anti-fibrotic agent. In certain embodiments, an anti-fibrotic agent is a modified oligonucleotide complementary to miR-21.

In certain embodiments, an additional therapy is dialysis. In certain embodiments, an additional therapy is kidney transplant.

In certain embodiments, pharmaceutical agents include anti-inflammatory agents. In certain embodiments, an anti-inflammatory agent is a steroidal anti-inflammatory agent. In certain embodiments, a steroid anti-inflammatory agent is a corticosteroid. In certain embodiments, a corticosteroid is prednisone. In certain embodiments, an anti-inflammatory agent is a non-steroidal anti-inflammatory drug. In certain embodiments, a non-steroidal anti-inflammatory agent is ibuprofen, a COX-I inhibitor, or a COX-2 inhibitor.

In certain embodiments, a pharmaceutical agent is a pharmaceutical agent that blocks one or more responses to fibrogenic signals.

In certain embodiments, an additional therapy may be a pharmaceutical agent that enhances the body's immune system, including low-dose cyclophosphamide, thymostimulin, vitamins and nutritional supplements (e.g., antioxidants, including vitamins A, C, E, beta-carotene, zinc, selenium, glutathione, coenzyme Q-10 and echinacea), and vaccines, e.g., the immunostimulating complex (ISCOM), which comprises a vaccine formulation that combines a multimeric presentation of antigen and an adjuvant.

In certain embodiments, the additional therapy is selected to treat or ameliorate a side effect of one or more pharmaceutical compositions of the present invention. Such side effects include, without limitation, injection site reactions, liver function test abnormalities, kidney function abnormalities, liver toxicity, renal toxicity, central nervous system abnormalities, and myopathies. For example, increased aminotransferase levels in serum may indicate liver toxicity or liver function abnormality. For example, increased bilirubin may indicate liver toxicity or liver function abnormality.

Certain MicroRNA Nucleobase Sequences

The modified oligonucleotides described herein have a nucleobase sequence that is complementary to miR-17 (SEQ ID NO: 1), or a precursor thereof (SEQ ID NO: 2). In certain embodiments, each nucleobase of the modified oligonucleotide is capable of undergoing base-pairing with a nucleobase at each corresponding position in the nucleobase sequence of miR-17, or a precursor thereof. In certain embodiments the nucleobase sequence of a modified oligonucleotide may have one or more mismatched base pairs with respect to the nucleobase sequence of miR-17 or precursor sequence, and remains capable of hybridizing to its target sequence.

As the miR-17 sequence is contained within the miR-17 precursor sequence, a modified oligonucleotide having a nucleobase sequence complementary to miR-17 is also complementary to a region of the miR-17 precursor.

In certain embodiments, a modified oligonucleotide consists of a number of linked nucleosides that is equal to the length of miR-17.

In certain embodiments, the number of linked nucleosides of a modified oligonucleotide is less than the length of miR-17. A modified oligonucleotide having a number of linked nucleosides that is less than the length of miR-17, wherein each nucleobase of the modified oligonucleotide is complementary to each nucleobase at a corresponding position of miR-17, is considered to be a modified oligonucleotide having a nucleobase sequence that is fully complementary to a region of the miR-17 sequence. For example, a modified oligonucleotide consisting of 19 linked nucleosides, where each nucleobase is complementary to a corresponding position of miR-17 that is 22 nucleobases in length, is fully complementary to a 19 nucleobase region of miR-17. Such a modified oligonucleotide has 100% complementarity to (or is fully complementary to) a 19 nucleobase segment of miR-17, and is considered to be 100% complementary to (or fully complementary to) miR-17.

In certain embodiments, a modified oligonucleotide comprises a nucleobase sequence that is complementary to a seed sequence, i.e. a modified oligonucleotide comprises a seed-match sequence. In certain embodiments, a seed sequence is a hexamer seed sequence. In certain such embodiments, a seed sequence is nucleobases 1-6 of miR-17. In certain such embodiments, a seed sequence is nucleobases 2-7 of miR-17. In certain such embodiments, a seed sequence is nucleobases 3-8 of miR-17. In certain embodiments, a seed sequence is a heptamer seed sequence. In certain such embodiments, a heptamer seed sequence is nucleobases 1-7 of miR-17. In certain such embodiments, a heptamer seed sequence is nucleobases 2-8 of miR-17. In certain embodiments, the seed sequence is an octamer seed sequence. In certain such embodiments, an octamer seed sequence is nucleobases 1-8 of miR-17. In certain embodiments, an octamer seed sequence is nucleobases 2-9 of miR-17.

miR-17 is a member of a family of microRNAs known as the miR-17 family. The miR-17 family includes miR-17, miR-20a, miR-20b, miR-93, miR-106a, and miR-106b. Each member of the miR-17 family has a nucleobase sequence comprising the nucleobase sequence 5'-AAAGUG-3,' or the miR-17 seed region, which is the nucleobase sequence at positions 2 through 7 of SEQ ID NO: 1. Additionally, each member of the miR-17 family shares some nucleobase sequence identity outside the seed region. Accordingly, a modified oligonucleotide complementary to miR-17 may target microRNAs of the miR-17 family, in addition to miR-17. In certain embodiments, a modified oligonucleotide targets two or more microRNAs of the miR-17 family. In certain embodiments, a modified oligonucleotide targets three or more microRNAs of the miR-17 family. In certain embodiments, a modified oligonucleotide targets four or more microRNAs of the miR-17 family. In certain embodiments, a modified oligonucleotide targets five or more microRNAs of the miR-17 family. In certain embodiments, a modified oligonucleotide targets six of the microRNAs of the miR-17 family.

In certain embodiments, a modified oligonucleotide comprises the nucleobase sequence 5'-GCACTTTG-3' (SEQ ID NO: 3). In certain embodiments, a modified oligonucleotide comprises the nucleobase sequence 5'-AGCACTTT-3' (SEQ ID NO: 4). In certain embodiments, a modified oligonucleotide comprises the nucleobase sequence 5'-AGCACTTTG-3' (SEQ ID NO: 5). In certain embodiments, a modified oligonucleotide comprises the nucleobase sequence 5'-AAGCACTTTG-3' (SEQ ID NO: 6). In certain embodiments, a modified oligonucleotide comprises the nucleobase sequence 5'-TAAGCACTTTG-3' (SEQ ID NO: 7). In certain embodiments, a modified oligonucleotide comprises the nucleobase sequence 5'-GTAAGCACTTTG-3' (SEQ ID NO: 8). In certain embodiments, a modified oligonucleotide comprises the nucleobase sequence 5'-TGTAAGCACTTTG-3' (SEQ ID NO: 9). In certain embodiments, a modified oligonucleotide comprises the nucleobase sequence 5'-CTGTAAGCACTTTG-3' (SEQ ID NO: 10). In certain embodiments, a modified oligonucleotide comprises the nucleobase sequence 5'-ACTGTAAGCACTTTG-3' (SEQ ID NO: 11). In certain embodiments, a modified oligonucleotide comprises the nucleobase sequence 5'-CACTGTAAGCACTTTG-3' (SEQ ID NO: 12). In certain embodiments, a modified oligonucleotide comprises the nucleobase sequence 5'-GCACTGTAAGCACTTTG-3' (SEQ ID NO: 13). In certain embodiments, a modified oligonucleotide comprises the nucleobase sequence 5'-TGCACTGTAAGCACTTTG-3' (SEQ ID NO: 14). In certain embodiments, a modified oligonucleotide comprises the nucleobase sequence 5'-CTGCACTGTAAGCACTTTG-3' (SEQ ID NO: 15). In certain embodiments, a modified oligonucleotide comprises the nucleobase sequence 5'-CCTGCACTGTAAGCACTTTG-3' (SEQ ID NO: 16). In certain embodiments, a modified oligonucleotide comprises the nucleobase sequence 5'-ACCTGCACTGTAAGCACTTTG-3' (SEQ ID NO: 17). In certain embodiments, a modified oligonucleotide comprises the nucleobase sequence 5'-CACCTGCACTGTAAGCACTTTG-3' (SEQ ID NO: 18). In certain embodiments, a modified oligonucleotide comprises the nucleobase sequence 5'-CTACCTGCACTGTAAGCACTTTG-3' (SEQ ID NO: 19). In any of these embodiments, the modified oligonucleotide consists of a nucleobase sequence selected from any one of SEQ ID Nos 3, 4, 5, 6, 7, 8, 9, 10, 11, 12, 13, 14, 15, 16, 17, and 18. In each nucleobase sequence, T is independently selected from a T and a U.

In certain embodiments, a modified oligonucleotide has a nucleobase sequence having one mismatch with respect to the nucleobase sequence of miR-17, or a precursor thereof. In certain embodiments, a modified oligonucleotide has a nucleobase sequence having two mismatches with respect to the nucleobase sequence of miR-17, or a precursor thereof. In certain such embodiments, a modified oligonucleotide has a nucleobase sequence having no more than two mismatches with respect to the nucleobase sequence of miR-17, or a precursor thereof. In certain such embodiments, the mismatched nucleobases are contiguous. In certain such embodiments, the mismatched nucleobases are not contiguous.

In certain embodiments, the number of linked nucleosides of a modified oligonucleotide is greater than the length of miR-17. In certain such embodiments, the nucleobase of an additional nucleoside is complementary to a nucleobase of the miR-17 stem-loop sequence. In certain embodiments, the number of linked nucleosides of a modified oligonucleotide is one greater than the length of miR-17. In certain such embodiments, the additional nucleoside is at the 5' terminus of an oligonucleotide. In certain such embodiments, the additional nucleoside is at the 3' terminus of an oligonucleotide. In certain embodiments, the number of linked nucleosides of a modified oligonucleotide is two greater than the length of miR-17. In certain such embodiments, the two additional nucleosides are at the 5' terminus of an oligonucleotide. In certain such embodiments, the two additional nucleosides are at the 3' terminus of an oligonucleotide. In certain such embodiments, one additional nucleoside is located at the 5' terminus and one additional nucleoside is located at the 3' terminus of an oligonucleotide. In certain embodiments, a region of the oligonucleotide may be fully complementary to the nucleobase sequence of miR-17, but the entire modified oligonucleotide is not fully complementary to miR-17. For example, a modified oligonucleotide consisting of 24 linked nucleosides, where the nucleobases of nucleosides 1 through 22 are each complementary to a corresponding position of miR-17 that is 22 nucleobases in length, has a 22 nucleoside portion that is fully complementary to the nucleobase sequence of miR-17 and approximately 92% overall complementarity to the nucleobase sequence of miR-17.

Certain Modified Oligonucleotides

In certain embodiments, a modified oligonucleotide consists of 8 to 25 linked nucleosides. In certain embodiments, a modified oligonucleotide consists of 8 to 12 linked nucleosides. In certain embodiments, a modified oligonucleotide consists of 12 to 25 linked nucleosides. In certain embodiments, a modified oligonucleotide consists of 15 to 25 linked nucleosides. In certain embodiments, a modified oligonucleotide consists of 15 to 19 linked nucleosides. In certain embodiments, a modified oligonucleotide consists of 15 to 16 linked nucleosides. In certain embodiments, a modified oligonucleotide consists of 17 to 23 linked nucleosides. In certain embodiments, a modified oligonucleotide consists of 19 to 23 linked nucleosides.

In certain embodiments, a modified oligonucleotide consists of 8 linked nucleosides. In certain embodiments, a modified oligonucleotide consists of 9 linked nucleosides. In certain embodiments, a modified oligonucleotide consists of 10 linked nucleosides. In certain embodiments, a modified oligonucleotide consists of 11 linked nucleosides. In certain embodiments, a modified oligonucleotide consists of 12 linked nucleosides. In certain embodiments, a modified oligonucleotide consists of 13 linked nucleosides. In certain embodiments, a modified oligonucleotide consists of 14 linked nucleosides. In certain embodiments, a modified oligonucleotide consists of 15 linked nucleosides. In certain embodiments, a modified oligonucleotide consists of 16 linked nucleosides. In certain embodiments, a modified oligonucleotide consists of 17 linked nucleosides. In certain embodiments, a modified oligonucleotide consists of 18 linked nucleosides. In certain embodiments, a modified oligonucleotide consists of 19 linked nucleosides. In certain embodiments, a modified oligonucleotide consists of 20 linked nucleosides. In certain embodiments, a modified oligonucleotide consists of 21 linked nucleosides. In certain embodiments, a modified oligonucleotide consists of 22 linked nucleosides. In certain embodiments, a modified oligonucleotide consists of 23 linked nucleosides. In certain embodiments, a modified oligonucleotide consists of 24 linked nucleosides. In certain embodiments, a modified oligonucleotide consists of 25 linked nucleosides.

In certain embodiments, a modified oligonucleotide comprises one or more 5-methylcytosines. In certain embodiments, each cytosine of a modified oligonucleotide comprises a 5-methylcytosine.

Certain Modifications

In certain embodiments, oligonucleotides provided herein may comprise one or more modifications to a nucleobase, sugar, and/or internucleoside linkage, and as such is a modified oligonucleotide. A modified nucleobase, sugar, and/or internucleoside linkage may be selected over an unmodified form because of desirable properties such as, for example, enhanced cellular uptake, enhanced affinity for other oligonucleotides or nucleic acid targets and increased stability in the presence of nucleases.

In certain embodiments, a modified oligonucleotide comprises one or more modified nucleosides. In certain such embodiments, a modified nucleoside is a stabilizing nucleoside. An example of a stabilizing nucleoside is a sugar-modified nucleoside.

In certain embodiments, a modified nucleoside is a sugar-modified nucleoside. In certain such embodiments, the sugar-modified nucleosides can further comprise a natural or modified heterocyclic base moiety and/or a natural or modified internucleoside linkage and may include further modifications independent from the sugar modification. In certain embodiments, a sugar modified nucleoside is a 2'-modified nucleoside, wherein the sugar ring is modified at the 2' carbon from natural ribose or 2'-deoxy-ribose.

In certain embodiments, a 2'-modified nucleoside has a bicyclic sugar moiety. In certain such embodiments, the bicyclic sugar moiety is a D sugar in the alpha configuration. In certain such embodiments, the bicyclic sugar moiety is a D sugar in the beta configuration. In certain such embodiments, the bicyclic sugar moiety is an L sugar in the alpha configuration. In certain such embodiments, the bicyclic sugar moiety is an L sugar in the beta configuration.

Nucleosides comprising such bicyclic sugar moieties are referred to as bicyclic nucleosides or BNAs. In certain embodiments, bicyclic nucleosides include, but are not limited to, (A) α-L-Methyleneoxy (4'-CH$_2$—O—2') BNA; (B) β-D-Methyleneoxy (4'-CH$_2$—O—2') BNA; (C) Ethyleneoxy (4'-(CH$_2$)$_2$—O—2') BNA; (D) Aminooxy (4'-CH$_2$—O—N(R)-2') BNA; (E) Oxyamino (4'-CH$_2$—N(R)—O—2') BNA; (F) Methyl(methyleneoxy) (4'-CH(CH$_3$)—O—2') BNA (also referred to as constrained ethyl or cEt); (G) methylene-thio (4'-CH$_2$—S—2') BNA; (H) methylene-amino (4'-CH$_2$—N(R)—2') BNA; (I) methyl carbocyclic (4'-CH$_2$—CH(CH$_3$)-2') BNA; (J) c-MOE (4'-CH(CH$_2$—OMe)-O—2') BNA and (K) propylene carbocyclic (4'-(CH$_2$)$_3$-2') BNA as depicted below.

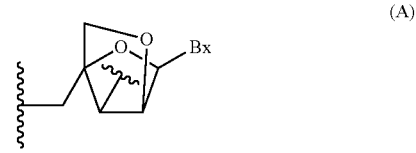

(A)

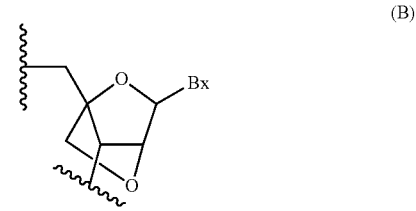

(B)

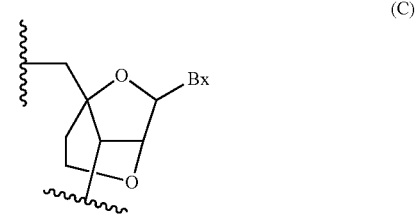

(C)

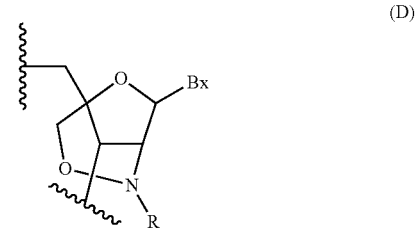

(D)

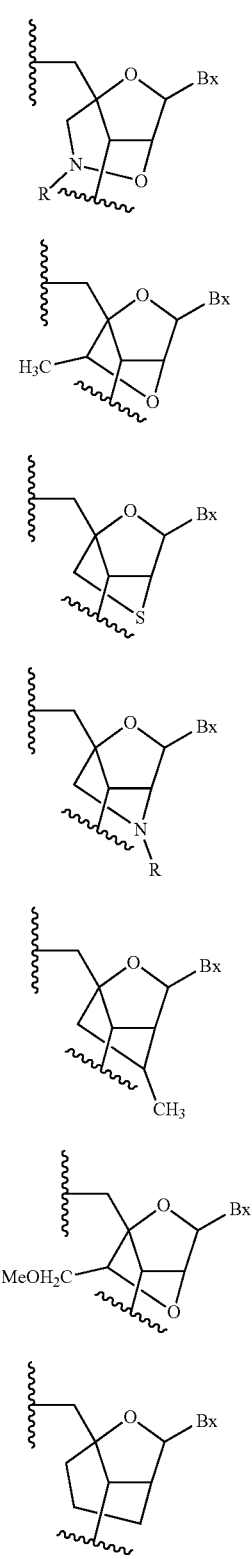

(E), (F), (G), (H), (I), (J), (K)

wherein Bx is a nucleobase moiety and R is, independently, H, a protecting group, or C₁-C₁₂ alkyl.

In certain embodiments, a 2'-modified nucleoside comprises a 2'-substituent group selected from F, OCF₃, O—CH₃, OCH₂CH₂OCH₃, 2'-O(CH₂)₂SCH₃, O—(CH₂)₂—O—N(CH₃)₂, —O(CH₂)₂O(CH₂)₂N(CH₃)₂, and O—CH₂—C(=O)—N(H)CH₃.

In certain embodiments, a 2'-modified nucleoside comprises a 2'-substituent group selected from F, O—CH₃, and OCH₂CH₂OCH₃.

In certain embodiments, a sugar-modified nucleoside is a 4'-thio modified nucleoside. In certain embodiments, a sugar-modified nucleoside is a 4'-thio-2'-modified nucleoside. A 4'-thio modified nucleoside has a β-D-ribonucleoside where the 4'-O replaced with 4'-S. A 4'-thio-2'-modified nucleoside is a 4'-thio modified nucleoside having the 2'—OH replaced with a 2'-substituent group. Suitable 2'-substituent groups include 2'—OCH₃, 2'-O—(CH₂)₂—OCH₃, and 2'—F.

In certain embodiments, a modified oligonucleotide comprises one or more internucleoside modifications. In certain such embodiments, each internucleoside linkage of a modified oligonucleotide is a modified internucleoside linkage. In certain embodiments, a modified internucleoside linkage comprises a phosphorus atom.

In certain embodiments, a modified oligonucleotide comprises at least one phosphorothioate internucleoside linkage. In certain embodiments, each internucleoside linkage of a modified oligonucleotide is a phosphorothioate internucleoside linkage.

In certain embodiments, a modified oligonucleotide comprises one or more modified nucleobases. In certain embodiments, a modified nucleobase is selected from 5-hydroxymethyl cytosine, 7-deazaguanine and 7-deazaadenine. In certain embodiments, a modified nucleobase is selected from 7-deaza-adenine, 7-deazaguanosine, 2-aminopyridine and 2-pyridone. In certain embodiments, a modified nucleobase is selected from 5-substituted pyrimidines, 6-azapyrimidines and N-2, N-6 and O-6 substituted purines, including 2 aminopropyladenine, 5-propynyluracil and 5-propynylcytosine.

In certain embodiments, a modified nucleobase comprises a polycyclic heterocycle. In certain embodiments, a modified nucleobase comprises a tricyclic heterocycle. In certain embodiments, a modified nucleobase comprises a phenoxazine derivative. In certain embodiments, the phenoxazine can be further modified to form a nucleobase known in the art as a G-clamp.

In certain embodiments, a modified oligonucleotide is conjugated to one or more moieties which enhance the activity, cellular distribution or cellular uptake of the resulting antisense oligonucleotides. In certain such embodiments, the moiety is a cholesterol moiety. In certain embodiments, the moiety is a lipid moiety. Additional moieties for conjugation include carbohydrates, phospholipids, biotin, phenazine, folate, phenanthridine, anthraquinone, acridine, fluoresceins, rhodamines, coumarins, and dyes. In certain embodiments, the carbohydrate moiety is N-acetyl-D-galactosamine (GalNac). In certain embodiments, a conjugate group is attached directly to an oligonucleotide. In certain embodiments, a conjugate group is attached to a modified oligonucleotide by a linking moiety selected from amino, hydroxyl, carboxylic acid, thiol, unsaturations (e.g., double or triple bonds), 8-amino-3,6-dioxaoctanoic acid (ADO), succinimidyl 4-(N-maleimidomethyl) cyclohexane-1-carboxylate (SMCC), 6-aminohexanoic acid (AHEX or AHA), substituted C1-C10 alkyl, substituted or unsubstituted C2-C10 alkenyl, and substituted or unsubstituted C2-C10 alkynyl. In certain such embodiments, a substituent group is selected from hydroxyl, amino, alkoxy, carboxy, benzyl, phenyl, nitro, thiol, thioalkoxy, halogen, alkyl, aryl, alkenyl and alkynyl.

In certain such embodiments, the compound comprises a modified oligonucleotide having one or more stabilizing groups that are attached to one or both termini of a modified oligonucleotide to enhance properties such as, for example, nuclease stability. Included in stabilizing groups are cap structures. These terminal modifications protect a modified oligonucleotide from exonuclease degradation, and can help in delivery and/or localization within a cell. The cap can be present at the 5'-terminus (5'-cap), or at the 3'-terminus (3'-cap), or can be present on both termini. Cap structures include, for example, inverted deoxy abasic caps.

Certain Pharmaceutical Compositions

Provided herein are pharmaceutical compositions. In certain embodiments, a pharmaceutical composition provided herein comprises a compound comprising a modified oligonucleotide consisting of 8 to 25 linked nucleosides and having a nucleobase sequence complementary to miR-17. In certain embodiments, a pharmaceutical composition provided herein comprises a compound consisting of a modified oligonucleotide consisting of 8 to 12 linked nucleosides and having a nucleobase sequence complementary to miR-17. In certain embodiments, a pharmaceutical composition provided herein comprises a compound comprising a modified oligonucleotide consisting of 15 to 25 linked nucleosides and having a nucleobase sequence complementary to miR-17. In certain embodiments, a pharmaceutical composition provided herein comprises a compound comprising a modified oligonucleotide consisting of 17 to 23 linked nucleosides and having a nucleobase sequence complementary to miR-17.

Suitable administration routes include, but are not limited to, oral, rectal, transmucosal, intestinal, enteral, topical, suppository, through inhalation, intrathecal, intracardiac, intraventricular, intraperitoneal, intranasal, intraocular, intratumoral, and parenteral (e.g., intravenous, intramuscular, intramedullary, and subcutaneous). In certain embodiments, pharmaceutical intrathecals are administered to achieve local rather than systemic exposures. For example, pharmaceutical compositions may be injected directly in the area of desired effect (e.g., into the kidney).

In certain embodiments, a pharmaceutical composition is administered in the form of a dosage unit (e.g., tablet, capsule, bolus, etc.). In some embodiments, a pharmaceutical compositions comprises a modified oligonucleotide at a dose within a range selected from 25 mg to 800 mg, 25 mg to 700 mg, 25 mg to 600 mg, 25 mg to 500 mg, 25 mg to 400 mg, 25 mg to 300 mg, 25 mg to 200 mg, 25 mg to 100 mg, 100 mg to 800 mg, 200 mg to 800 mg, 300 mg to 800 mg, 400 mg to 800 mg, 500 mg to 800 mg, 600 mg to 800 mg, 100 mg to 700 mg, 150 mg to 650 mg, 200 mg to 600 mg, 250 mg to 550 mg, 300 mg to 500 mg, 300 mg to 400 mg, and 400 mg to 600 mg. In certain embodiments, such pharmaceutical compositions comprise a modified oligonucleotide in a dose selected from 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 105 mg, 110 mg, 115 mg, 120 mg, 125 mg, 130 mg, 135 mg, 140 mg, 145 mg, 150 mg, 155 mg, 160 mg, 165 mg, 170 mg, 175 mg, 180 mg, 185 mg, 190 mg, 195 mg, 200 mg, 205 mg, 210 mg, 215 mg, 220 mg, 225 mg, 230 mg, 235 mg, 240 mg, 245 mg, 250 mg, 255 mg, 260 mg, 265 mg, 270 mg, 270 mg, 280 mg, 285 mg, 290 mg, 295 mg, 300 mg, 305 mg, 310 mg, 315 mg, 320 mg, 325 mg, 330 mg, 335 mg, 340 mg, 345 mg, 350 mg, 355 mg, 360 mg, 365 mg, 370 mg, 375 mg, 380 mg, 385 mg, 390 mg, 395 mg, 400 mg, 405 mg, 410 mg, 415 mg, 420 mg, 425 mg, 430 mg, 435 mg, 440 mg, 445 mg, 450 mg, 455 mg, 460 mg, 465 mg, 470 mg, 475 mg, 480 mg, 485 mg, 490 mg, 495 mg, 500 mg, 505 mg, 510 mg, 515 mg, 520 mg, 525 mg, 530 mg, 535 mg, 540 mg, 545 mg, 550 mg, 555 mg, 560 mg, 565 mg, 570 mg, 575 mg, 580 mg, 585 mg, 590 mg, 595 mg, 600 mg, 605 mg, 610 mg, 615 mg, 620 mg, 625 mg, 630 mg, 635 mg, 640 mg, 645 mg, 650 mg, 655 mg, 660 mg, 665 mg, 670 mg, 675 mg, 680 mg, 685 mg, 690 mg, 695 mg, 700 mg, 705 mg, 710 mg, 715 mg, 720 mg, 725 mg, 730 mg, 735 mg, 740 mg, 745 mg, 750 mg, 755 mg, 760 mg, 765 mg, 770 mg, 775 mg, 780 mg, 785 mg, 790 mg, 795 mg, and 800 mg. In certain such embodiments, a pharmaceutical composition of the comprises a dose of modified oligonucleotide selected from 25 mg, 50 mg, 75 mg, 100 mg, 150 mg, 200 mg, 250 mg, 300 mg, 350 mg, 400 mg, 500 mg, 600 mg, 700 mg, and 800 mg.

In certain embodiments, a pharmaceutical agent is sterile lyophilized modified oligonucleotide that is reconstituted with a suitable diluent, e.g., sterile water for injection or sterile saline for injection. The reconstituted product is administered as a subcutaneous injection or as an intravenous infusion after dilution into saline. The lyophilized drug product consists of a modified oligonucleotide which has been prepared in water for injection, or in saline for injection, adjusted to pH 7.0-9.0 with acid or base during preparation, and then lyophilized. The lyophilized modified oligonucleotide may be 25-800 mg of an oligonucleotide. It is understood that this encompasses 25, 50, 75, 100, 125, 150, 175, 200, 225, 250, 275, 300, 325, 350, 375, 425, 450, 475, 500, 525, 550, 575, 600, 625, 650, 675, 700, 725, 750, 775, and 800 mg of modified lyophilized oligonucleotide. Further, in some embodiments, the lyophilized modified oligonucleotide is an amount of an oligonucleotide within a range selected from 25 mg to 800 mg, 25 mg to 700 mg, 25 mg to 600 mg, 25 mg to 500 mg, 25 mg to 400 mg, 25 mg to 300 mg, 25 mg to 200 mg, 25 mg to 100 mg, 100 mg to 800 mg, 200 mg to 800 mg, 300 mg to 800 mg, 400 mg to 800 mg, 500 mg to 800 mg, 600 mg to 800 mg, 100 mg to 700 mg, 150 mg to 650 mg, 200 mg to 600 mg, 250 mg to 550 mg, 300 mg to 500 mg, 300 mg to 400 mg, and 400 mg to 600 mg. The lyophilized drug product may be packaged in a 2 mL Type I, clear glass vial (ammonium sulfate-treated), stoppered with a bromobutyl rubber closure and sealed with an aluminum FLIP-OFF® overseal.

In certain embodiments, the pharmaceutical compositions provided herein may additionally contain other adjunct components conventionally found in pharmaceutical compositions, at their art-established usage levels. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the oligonucleotide(s) of the formulation.

Lipid moieties have been used in nucleic acid therapies in a variety of methods. In one method, the nucleic acid is introduced into preformed liposomes or lipoplexes made of mixtures of cationic lipids and neutral lipids. In another method, DNA complexes with mono- or poly-cationic lipids are formed without the presence of a neutral lipid. In certain embodiments, a lipid moiety is selected to increase distribution of a pharmaceutical agent to a particular cell or tissue. In certain embodiments, a lipid moiety is selected to increase distribution of a pharmaceutical agent to fat tissue. In certain embodiments, a lipid moiety is selected to increase distribution of a pharmaceutical agent to muscle tissue.

In certain embodiments, INTRALIPID is used to prepare a pharmaceutical composition comprising an oligonucleotide. Intralipid is fat emulsion prepared for intravenous administration. It is made up of 10% soybean oil, 1.2% egg yolk phospholipids, 2.25% glycerin, and water for injection. In addition, sodium hydroxide has been added to adjust the pH so that the final product pH range is 6 to 8.9.

In certain embodiments, a pharmaceutical composition provided herein comprise a polyamine compound or a lipid moiety complexed with a nucleic acid. In certain embodiments, such preparations comprise one or more compounds each individually having a structure defined by formula (Z) or a pharmaceutically acceptable salt thereof,

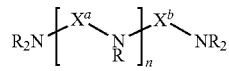

wherein each $X^a$ and $X^b$, for each occurrence, is independently $C_{1-6}$ alkylene; n is 0, 1, 2, 3, 4, or 5; each R is independently H, wherein at least n+2 of the R moieties in at least about 80% of the molecules of the compound of formula (Z) in the preparation are not H; m is 1, 2, 3 or 4; Y is O, $NR^2$, or S; $R^1$ is alkyl, alkenyl, or alkynyl; each of which is optionally substituted with one or more substituents; and $R^2$ is H, alkyl, alkenyl, or alkynyl; each of which is optionally substituted each of which is optionally substituted with one or more substituents; provided that, if n=0, then at least n+3 of the R moieties are not H. Such preparations are described in PCT publication WO/2008/042973, which is herein incorporated by reference in its entirety for the disclosure of lipid preparations. Certain additional preparations are described in Akinc et al., *Nature Biotechnology* 26, 561-569 (1 May 2008), which is herein incorporated by reference in its entirety for the disclosure of lipid preparations.

In certain embodiments, pharmaceutical compositions provided herein comprise one or more modified oligonucleotides and one or more excipients. In certain such embodiments, excipients are selected from water, salt solutions, alcohol, polyethylene glycols, gelatin, lactose, amylase, magnesium stearate, talc, silicic acid, viscous paraffin, hydroxymethylcellulose and polyvinylpyrrolidone.

In certain embodiments, a pharmaceutical composition provided herein is prepared using known techniques, including, but not limited to mixing, dissolving, granulating, dragee-making, levigating, emulsifying, encapsulating, entrapping or tableting processes.

In certain embodiments, a pharmaceutical composition provided herein is a liquid (e.g., a suspension, elixir and/or solution). In certain of such embodiments, a liquid pharmaceutical composition is prepared using ingredients known in the art, including, but not limited to, water, glycols, oils, alcohols, flavoring agents, preservatives, and coloring agents.

In certain embodiments, a pharmaceutical composition provided herein is a solid (e.g., a powder, tablet, and/or capsule). In certain of such embodiments, a solid pharmaceutical composition comprising one or more oligonucleotides is prepared using ingredients known in the art, including, but not limited to, starches, sugars, diluents, granulating agents, lubricants, binders, and disintegrating agents.

In certain embodiments, a pharmaceutical composition provided herein is formulated as a depot preparation. Certain such depot preparations are typically longer acting than non-depot preparations. In certain embodiments, such preparations are administered by implantation (for example subcutaneously or intramuscularly) or by intramuscular injection. In certain embodiments, depot preparations are prepared using suitable polymeric or hydrophobic materials (for example an emulsion in an acceptable oil) or ion exchange resins, or as sparingly soluble derivatives, for example, as a sparingly soluble salt.

In certain embodiments, a pharmaceutical composition provided herein comprises a delivery system. Examples of delivery systems include, but are not limited to, liposomes and emulsions. Certain delivery systems are useful for preparing certain pharmaceutical compositions including those comprising hydrophobic compounds. In certain embodiments, certain organic solvents such as dimethylsulfoxide are used.

In certain embodiments, a pharmaceutical composition provided herein comprises one or more tissue-specific delivery molecules designed to deliver the one or more pharmaceutical agents of the present invention to specific tissues or cell types. For example, in certain embodiments, pharmaceutical compositions include liposomes coated with a tissue-specific antibody.

In certain embodiments, a pharmaceutical composition provided herein comprises a sustained-release system. A non-limiting example of such a sustained-release system is a semi-permeable matrix of solid hydrophobic polymers. In certain embodiments, sustained-release systems may, depending on their chemical nature, release pharmaceutical agents over a period of hours, days, weeks or months.

In certain embodiments, a pharmaceutical composition is prepared for administration by injection (e.g., intravenous, subcutaneous, intramuscular, etc.). In certain of such embodiments, a pharmaceutical composition comprises a carrier and is formulated in aqueous solution, such as water or physiologically compatible buffers such as Hanks's solution, Ringer's solution, or physiological saline buffer. In certain embodiments, other ingredients are included (e.g., ingredients that aid in solubility or serve as preservatives). In certain embodiments, injectable suspensions are prepared using appropriate liquid carriers, suspending agents and the like. Certain pharmaceutical compositions for injection are presented in unit dosage form, e.g., in ampoules or in multi-dose containers. Certain pharmaceutical compositions for injection are suspensions, solutions or emulsions in oily or aqueous vehicles, and may contain formulatory agents such as suspending, stabilizing and/or dispersing agents. Certain solvents suitable for use in pharmaceutical compositions for injection include, but are not limited to, lipophilic solvents and fatty oils, such as sesame oil, synthetic fatty acid esters, such as ethyl oleate or triglycerides, and liposomes. Aqueous injection suspensions may contain substances that increase the viscosity of the suspension, such as sodium carboxymethyl cellulose, sorbitol, or dextran. Optionally, such suspensions may also contain suitable stabilizers or agents that increase the solubility of the pharmaceutical agents to allow for the preparation of highly concentrated solutions.

In certain embodiments, a pharmaceutical composition provided herein comprises a modified oligonucleotide in a therapeutically effective amount. In certain embodiments, the therapeutically effective amount is sufficient to prevent, alleviate or ameliorate symptoms of a disease or to prolong the survival of the subject being treated. Determination of a therapeutically effective amount is well within the capability of those skilled in the art.

In certain embodiments, one or more modified oligonucleotides provided herein is formulated as a prodrug. In certain embodiments, upon in vivo administration, a prodrug is chemically converted to the biologically, pharmaceutically or therapeutically more active form of an oligonucleotide. In certain embodiments, prodrugs are useful because they are easier to administer than the corresponding active form. For example, in certain instances, a prodrug may be more bioavailable (e.g., through oral administration) than is the corresponding active form. In certain instances, a prodrug may have improved solubility compared to the corresponding active form. In certain embodiments, prodrugs are less water soluble than the corresponding active form. In certain instances, such prodrugs possess superior transmittal across cell membranes, where water solubility is detrimental to mobility. In certain embodiments, a prodrug is an ester. In certain such embodiments, the ester is metabolically hydrolyzed to carboxylic acid upon administration. In certain instances the carboxylic acid containing compound is the corresponding active form. In certain embodiments, a prodrug comprises a short peptide (polyaminoacid) bound to an acid group. In certain of such embodiments, the peptide is cleaved upon administration to form the corresponding active form.

In certain embodiments, a prodrug is produced by modifying a pharmaceutically active compound such that the active compound will be regenerated upon in vivo administration. The prodrug can be designed to alter the metabolic stability or the transport characteristics of a drug, to mask side effects or toxicity, to improve the flavor of a drug or to alter other characteristics or properties of a drug. By virtue of knowledge of pharmacodynamic processes and drug metabolism in vivo, those of skill in this art, once a pharmaceutically active compound is known, can design prodrugs of the compound (see, e.g., Nogrady (1985) Medicinal Chemistry A Biochemical Approach, Oxford University Press, New York, pages 388-392).

Certain Kits

The present invention also provides kits. In some embodiments, the kits comprise one or more compounds of the invention comprising a modified oligonucleotide, wherein the nucleobase sequence of the oligonucleotide is complementary to the nucleobase sequence of miR-17. The compounds can have any of the nucleoside patterns described herein. In some embodiments, the compounds can be present within a vial. A plurality of vials, such as 10, can be present in, for example, dispensing packs. In some embodiments, the vial is manufactured so as to be accessible with a syringe. The kit can also contain instructions for using the compounds.

In some embodiments, the kits may be used for administration of the compound to a subject. In such instances, in addition to compounds comprising a modified oligonucleotide complementary to miR-17, the kit can further comprise one or more of the following: syringe, alcohol swab, cotton ball, and/or gauze pad. In some embodiments, the compounds can be present in a pre-filled syringe (such as a single-dose syringes with, for example, a 27 gauge, ½ inch needle with a needle guard), rather than in a vial. A plurality of pre-filled syringes, such as 10, can be present in, for example, dispensing packs. The kit can also contain instructions for administering the compounds comprising a modified oligonucleotide complementary to miR-17.

Certain Experimental Models

In certain embodiments, the present invention provides methods of using and/or testing modified oligonucleotides of the present invention in an experimental model. Those having skill in the art are able to select and modify the protocols for such experimental models to evaluate a pharmaceutical agent of the invention.

Generally, modified oligonucleotides are first tested in cultured cells. Suitable cell types include those that are related to the cell type to which delivery of a modified oligonucleotide is desired in vivo. For example, suitable cell types for the study of the methods described herein include primary or cultured cells.

In certain embodiments, the extent to which a modified oligonucleotide interferes with the activity of miR-17 is assessed in cultured cells. In certain embodiments, inhibition of microRNA activity may be assessed by measuring the levels of the microRNA. Alternatively, the level of a predicted or validated microRNA-regulated transcript may be measured. An inhibition of microRNA activity may result in the increase in the miR-17-regulated transcript, and/or the protein encoded by miR-17-regulated transcript. Further, in certain embodiments, certain phenotypic outcomes may be measured.

Several animal models are available to the skilled artisan for the study of miR-17 in models of human disease. Models of polycystic kidney disease include, but are not limited to, models with mutations and/or deletions in Pkd1 and/or Pkd2; and models comprising mutations in other genes. Nonlimiting exemplary models of PKD comprising mutations and/or deletions in Pkd1 and/or Pkd2 include hypomorphic models, such as models comprising missense mutations in Pkd1 and models with reduced or unstable expression of Pkd2; inducible conditional knockout models; and conditional knockout models. Nonlimiting exemplary PKD models comprising mutations in genes other than Pkd1 and Pkd2 include models with mutations in Pkhd1, Nek8, Kif3a, and/or Nphp3. PKD models are reviewed, e.g., in Shibazaki et al., *Human Mol. Genet.*, 2008; 17(11): 1505-1516; Happe and Peters, *Nat Rev Nephrol.*, 2014; 10(10): 587-601; and Patel et al., *PNAS*, 2013; 110(26): 10765-10770.

Certain Quantitation Assays

In certain embodiments, microRNA levels are quantitated in cells or tissues in vitro or in vivo. In certain embodiments, changes in microRNA levels are measured by microarray analysis. In certain embodiments, changes in microRNA levels are measured by one of several commercially available PCR assays, such as the TaqMan☐ MicroRNA Assay (Applied Biosystems).

Modulation of microRNA activity with an anti-miR or microRNA mimic may be assessed by microarray profiling of mRNAs. The sequences of the mRNAs that are modulated (either increased or decreased) by the anti-miR or microRNA mimic are searched for microRNA seed sequences, to compare modulation of mRNAs that are targets of the microRNA to modulation of mRNAs that are not targets of the microRNA. In this manner, the interaction of the anti-miR with miR-17, or miR-17 mimic with its targets, can be evaluated. In the case of an anti-miR, mRNAs whose expression levels are increased are screened for the mRNA sequences that comprise a seed match to the microRNA to which the anti-miR is complementary.

Modulation of microRNA activity with an anti-miR-17 compound may be assessed by measuring the level of a mRNA target of miR-17, either by measuring the level of the mRNA itself, or the protein transcribed therefrom. Antisense inhibition of a microRNA generally results in the increase in the level of mRNA and/or protein of the mRNA target of the microRNA.

EXAMPLES

The following examples are presented in order to more fully illustrate some embodiments of the invention. They should in no way be construed, however, as limiting the broad scope of the invention.

Those of ordinary skill in the art will readily adopt the underlying principles of this discovery to design various compounds without departing from the spirit of the current invention.

Example 1

Anti-miR-17 in a Model of Polycystic Kidney Disease

Pkhd1/cre;Pkd2$^{F/F}$ mice spontaneously develop polycystic kidney disease, and were used as a model of ADPKD. See Patel et al., PNAS, 2013; 110(26): 10765-10770.

A modified oligonucleotide complementary to miR-17 (anti-miR-17 compound) was tested in the Pkhd1/cre; Pkd2$^{F/F}$ mouse model of ADPKD. Wild-type mice were used as control mice. An oligonucleotide complementary to a miRNA unrelated to miR-17 was used as a treatment control for specificity (anti-miR-control). The anti-miR-17 compound was a fully phosphorothioated oligonucleotide 19 linked nucleosides in length (5'-CTGCACTGTAAGCACTTTG-3'; SEQ ID NO: 15), with DNA, 2'-MOE and S-cEt sugar moieties.

From 10 to 12 days of age, sex-matched littermates of mice were treated with anti-miR-17 (20 mg/kg) or PBS, for a total of three daily doses. At 19 days of age, the mice were treated with a fourth dose of anti-miR-17 (20 mg/kg) or PBS. Anti-miR-17 was administered subcutaneously. (1) Pkhd1/cre;Pkd2$^{F/F}$ mice, PBS administration, n=8; (2) Pkhd1/cre;Pkd2$^{F/F}$ mice, anti-miR-control administration, n=8; (3) Pkhd1/cre;Pkd2$^{F/F}$ mice, anti-miR-17 administration, n=8. Mice were sacrificed at 28 days, and kidney weight, cyst index, kidney function, and kidney markers measured. Statistical significance was calculated by Welch's t-test.

The mean ratio of kidney weight to body weight in Pkhd1/cre;Pkd2$^{F/F}$ mice treated with anti-miR-17 was 17% lower than the mean ratio of kidney weight to body weight in Pkhd1/cre;Pkd2$^{F/F}$ mice administered anti-miR-control or PBS only (p=0.017). Pkhd1/cre;Pkd2$^{F/F}$ mice treated with anti-miR-17 showed a mean 6% reduction in cyst index compared to Pkhd1/cre;Pkd2$^{F/F}$ mice administered anti-miR-control or PBS, although the difference was not statistically significant (p=0.072). Cyst index is a histological measurement of cystic area relative to total kidney area. Mean serum creatinine levels in Pkhd1/cre;Pkd2$^{F/F}$ mice treated with anti-miR-17 were 25% lower than in Pkhd1/cre;Pkd2$^{F/F}$ mice administered anti-miR-control or PBS, although the result was not statistically significant (p=0.069). Kim1 expression was reduced by 33% in Pkhd1/cre;Pkd2$^{F/F}$ mice treated with anti-miR-17 versus anti-miR-control or PBS (p=0.024), and Ngal expression was reduced by 36% in Pkhd1/cre;Pkd2$^{F/F}$ mice treated with anti-miR-17 versus anti-miR-control or PBS (p=0.028). Finally, blood urea nitrogen (BUN) levels were reduced by 20% in Pkhd1/cre;Pkd2$^{F/F}$ mice treated with anti-miR-17 versus anti-miR-control or PBS (p=0.006). BUN is a blood marker of kidney function. Higher BUN correlates with poorer kidney function. A reduction in BUN is an indicator of reduced kidney injury and damage and improved function.

These results demonstrate that anti-miR-17 treatment leads to a positive outcome in Pkhd1/cre;Pkd2$^{F/F}$ mice in the primary treatment endpoint, kidney volume. Anti-miR-17 treatment also significantly reduced BUN and expression of kidney injury mRNA biomarkers, Kim1 and Ngal, in Pkhd1/cre;Pkd2$^{F/F}$ mice. Finally, anti-miR-17 treatment resulted in a trend toward reduced serum creatinine and reduced cyst index in the Pkhd1/cre;Pkd2$^{F/F}$ mice. These outcomes were not observed with anti-miR-control, indicating that they are specifically due to miR-17 inhibition.

Example 3

Anti-miR Distribution in the Kidney of Pkhd1/cre;Pkd2F/F Mice

Oligonucleotides, including anti-miR compounds, are known to distribute to several cell types within the kidney. As reported by Chau et al., Sci Transl Med., 2012, 121ra18, following administration of a Cy3-labeled anti-miR to either normal mice or mice subjected to kidney injury (unilateral ureteral obstruction, a model of interstitial fibrosis), the greatest fluorescence intensity in the kidney was in proximal tubule epithelium. The endothelium, pericytes, myofibroblasts, and macrophages also all contained detectable amounts of Cy3-labeled anti-miR. However, the glomerulus, in particular podocytes, did not appear to take up significant amounts of anti-miR consistent with the known distribution of chemically modified oligonucleotides (Masarjian et al., Oligonucleotides, 2004, 14, 299-310).

To investigate the distribution of anti-miR in a mouse model of polycystic kidney disease, anti-miR-17 compound was administered to two different groups of Pkhd1/cre; Pkd2$^{F/F}$ mice, one starting at 10 days of age (n=4; considered precystic) and one starting at 21 days of age (n=4; considered cystic) and to one group of wild type mice starting at 21 days of age (n=4). In each group, compound was administered at 20 mg/kg daily for three doses. Mice were sacrificed three days after the last dose and kidneys were harvested and processed for histological analysis. Anti-miR-17 was detected using an antibody that recognizes phosphorothioated oligonucleotides.

Sections of kidney tissue were stained with an antibody that recognizes phosphorothioated oligonucleotides as a marker for anti-miR-17 compound, or dolichos biflorus agglutinin (DBA) as a marker for collecting ducts. In all groups, the majority of the staining was found outside the collecting ducts, possibly in the proximal tubule epithelium. Anti-miR-17 was also delivered to collecting duct cysts even when administered after numerous cysts had already formed in the kidney. Staining in the collecting ducts appeared to be greater in cysts compared to normal collecting ducts, suggesting that delivery of compound may increase with disease state.

To confirm functional delivery, RT-qPCR was used to measure gene expression changes induced by anti-let-7 compound. A panel of 36 let-7 target genes showed significant increases in expression in both precystic and cystic kidneys of Pkhd1/cre;Pkd2$^{F/F}$ mice as well as from wild type mice administered with anti-let-7.

These results demonstrate that anti-miR compounds can successfully be delivered to cystic kidneys to inhibit miR-NAs.

Example 3

Inhibition of miR-17 Family Members

A number of microRNAs share seed sequence identity, and are thus members of a microRNA family. As the seed region of a microRNA is determining factor for target specificity, microRNA family members often regulate similar sets of messenger RNA targets. Outside the seed region, microRNA family members share varying degrees of sequence identity.

One such family is the miR-17 family, which includes miR-17, miR-20a, miR-20b, miR-93, miR-106a, and miR-106b. The individual microRNAs of this microRNA family are located on three different chromosomes, within three different microRNA clusters. miR-17 and miR-20a reside within the miR-17-92 cluster on human chromosome 13; miR-20b and miR-106a reside within the miR-106a-363 cluster on the human X chromosome, and miR-93 and miR-106b reside within the miR-106b-25 cluster on human chromosome 7 (FIG. 1A). Each of these three clusters contains other microRNAs that are not members of the miR-17 family, and thus do not comprise the miR-17 2-7 seed sequence. These microRNAs, however, are members of other miR families, as shown in FIG. 1B. The miR-17 family members are shown in FIG. 1B, with the miR-17 2-7 seed sequence in bold text. The seed sequence of the miR-18 family members (miR-18a and miR-18b) contains a one nucleobase difference relative to the miR-17 2-7 seed sequence, however outside the seed region the sequences are dissimilar.

Due to the sequence identity amongst microRNA family members, and because a modified oligonucleotide with less than 100% complementarity to a microRNA sequence may still inhibit the activity of that microRNA, a modified oligonucleotide with a nucleobase sequence 100% complementary to the nucleobase sequence of a first member of the family, and which is less than 100% complementary to one or more other members of the family, may inhibit those one or more other members of the family, in addition to inhibiting the activity of the first member of the microRNA family. For example, a modified oligonucleotide with a nucleobase sequence that is 100% complementary to miR-17 (5'-CTGCACTGTAAGCACTTTG-3'; SEQ ID NO: 15), and less than 100% complementarity to other members of the miR-17 family (Table 1), is expected to inhibit those other members of the miR-17 family.

TABLE 1

% Complementarity of anti-miR-17 to members of miR-17 family

| microRNA | SEQUENCE (5' TO 3') miR-17 2-7 seed in bold | # of complementanry nucleobases | % Complementarity | SEQ ID NO: |
|---|---|---|---|---|
| miR-17 | CAAAGUGCUUACAGUGCAGGUAG | 19 | 100% | 1 |
| miR-20a | UAAAGUGCUUAUAGUGCAGGUAG | 17 | 89.5% | 21 |
| miR-20b | CAAAGUGCUCAUAGUGCAGGUAG | 17 | 89.5% | 22 |
| miR-93 | CAAAGUGCUGUUCGUGCAGGUAG | 14 | 73.7% | 23 |
| miR-106a | AAAAGUGCUUACAGUGCAGGUAG | 17 | 89.5% | 24 |
| miR-106b | UAAAGUGCUGACAGUGCAGAU | 16 | 84.2% | 25 |

To test the inhibition of the miR-17 family members, the luciferase reporter assay was used. A luciferase reporter plasmid for each of miR-17, miR-20a, miR-20b, miR-93, and miR-106b was constructed, with a fully complementary microRNA binding site in the 3'-UTR of the luciferase gene. For each microRNA, HeLa cells were transfected with the microRNA mimic and its cognate luciferase reporter, followed by transfection with anti-miR-17. Each of miR-17, miR-20a, miR-20b, miR-93, and miR-106b was inhibited by the anti-miR-17 compound, demonstrating that the anti-miR-17 compound inhibits multiple members of the miR-17 family, even when there are mismatches present between the anti-miR-17 and microRNA sequences.

A separate assay, the microRNA polysome shift assay (miPSA), confirmed that the anti-miR-17 compound directly engages three members of the miR-17 family, miR-17, miR-20b and miR-106a (Androsavich et al., *Nucleic Acids Research*, 2015, 44: e13). The miPSA relies on the principle that active miRNAs bind to their mRNA targets in translationally active high molecular weight (HMW) polysomes, whereas the inhibited miRNAs reside in the low MW (LMW) polysomes. Treatment with anti-miR results in a shift of the microRNA from HMW polysomes to LMW polysomes. Thus, the miPSA provides a direct measurement of microRNA target engagement by a complementary anti-miR. Androsavich et al. further confirmed that non-miR-17 family miRNAs, on the other hand, were unresponsive in comparison, with one exception: miR-18a unexpectedly showed strong cross-reactivity at higher doses (which may be explained by the miR-17 and miR-18 seed sequences having only a single nucleotide A/G difference (FIG. 1).

Accordingly, treatment with an anti-miR-17 compound inhibits all members of the miR-17 family, even where there are mismatches present between the anti-miR-17 and microRNA sequences.

Example 4 miR-17 Inhibition in Human ADPKD Cysts

The effects of miR-17 inhibition were studied in primary cultures derived from human ADPKD cysts. Frozen human primary ADPKD cells were provided by the PKD Research Biomaterials and Cellular Models Core at the Kansas University Medical Center (KUMC). Human primary ADPKD cells were grown in DMEM:F12 medium (Gibco) supplemented with 5% FBS, 5 ug/ml insulin, 5 ug/ml transferrin and 5 ng/ml sodium selenite (ITS) (Lonza), as previously described (Yamaguchi et al., *Am J Physiol Renal Physiol,* 2010, 299: F944-951).

Proliferation Assay

At 80% confluency, human ADPKD cells were trypsinized using 1:10 dilution of Trypsin in $Ca^{+2}$ and $Mg^{+2}$ free PBS. Cells were transfected with RNAiMAX (Life Technologies) following the manufacturer's protocol at a density of 2500 cells/well in a 96-well plate. Treatments were as follows:

anti-miR-17 (at doses of 3 nM, 10 nM, or 30 nM; n=5 for each treatment)

control oligonucleotide (at doses indicated in Table 3; n=5 for each treatment). To vary the control treatments, two different control groups were used. For cultures derived from donors 1-4, 3 or 5 control oligonucleotides were tested, each at a single dose of 30 nM. For cells derived from donor 5, a single control oligonucleotide was tested at three different doses.

mock-transfection with RNAiMAX (n=5)

PBS (n=5)

Cell viability was measured using MTT assay (Promega) on day three following the manufacturer's protocol. Results are shown in Table 2. The mean for each anti-miR-17 treatment group or control oligonucleotide treatment group is normalized to the mean for the mock treatment group. Standard error of the mean is shown. Statistical analysis was performed using Student's t-test for pairwise comparisons or Analysis of variance (ANOVA) followed by Tukey's post hoc test for multiple comparison. P values are as follows: * indicates P<0.05, indicates P<0.01, *indicates P<0.005, and ****indicates P<0.001. For anti-miR-17 treatment, P-value indicates significance relative to mock treatment. For control oligonucleotide treatment, two different P-values are shown, one indicating significance relative to mock treatment (P-value 1 in Table 2) and the other indicating significance relative to anti-miR-17 30 nM treatment (P-value 2 in Table 2). N.t. indicates not tested.

Treatment with anti-miR-17 produced a dose-dependent reduction in the proliferation of cyst epithelia, relative to mock transfection treatment. Unlike treatment with anti-miR-17, the majority of control oligonucleotide treatments did not consistently reduce proliferation by a statistically significant amount.

As an example, treatment of cyst epithelial cultures from Donor 1 with 30 nM anti-miR-17 reduced cell proliferation by 47%, relative to mock transfection (P<0.0001), whereas treatment with control oligonucleotides did not reduce cell proliferation by a statistically significant amount. Further, for cyst epithelial cultures from the same donor, a comparison of anti-miR-17 30 nM treatment to each of the three control treatments also reveals a statistically significant reduction in cell proliferation by anti-miR-17 treatment (P<0.0001).

TABLE 2

Proliferation of cyst epithelia

| Mean per Donor | Treatment | | | | | Control Oligonucleotides | | | | |
|---|---|---|---|---|---|---|---|---|---|---|
| | | | anti-miR-17 | | | #1 | #2 | #3 | #4 | #5 |
| | PBS | Mock | 3 nM | 10 nM | 30 nM | 30 nM | 30 nM | 30 nM | 30 nM | 30 nM |
| Donor 1 mean | 1.94 | 1.00 | 0.98 | 0.89 | 0.53 | 1.09 | 0.94 | 1.15 | n.t. | n.t. |
| SEM | 0.03 | 0.05 | 0.03 | 0.02 | 0.01 | 0.04 | 0.06 | 0.04 | | |
| p-value 1 | | | ns | ns | **** | ns | ns | ns | | |
| p-value 2 | | | | | | **** | **** | **** | | |
| Donor 2 mean | 1.00 | 1.00 | 1.00 | 0.94 | 0.78 | 0.97 | 0.91 | 0.83 | 0.64 | 0.97 |
| SEM | 0.03 | 0.03 | 0.03 | 0.02 | 0.03 | 0.02 | 0.03 | 0.05 | 0.04 | 0.01 |
| p-value 1 | | | ns | ns | *** | ns | ns | * | **** | ns |
| p-value 2 | | | | | | ** | ns | ns | ns | ** |
| Donor 3 mean | 1.01 | 1.00 | 0.65 | 0.58 | 0.27 | 0.59 | 0.68 | 0.63 | 0.23 | 0.63 |
| SEM | 0.03 | 0.02 | 0.04 | 0.02 | 0.06 | 0.03 | 0.03 | 0.03 | 0.04 | 0.04 |
| p-value 1 | | | **** | **** | **** | **** | **** | **** | **** | **** |
| p-value 2 | | | | | | **** | **** | **** | ns | **** |
| Donor 4 mean | 1.36 | 1.00 | 0.75 | 0.62 | 0.17 | 0.74 | 0.67 | 0.57 | 0.40 | 0.29 |
| SEM | 0.05 | 0.07 | 0.03 | 0.05 | 0.01 | 0.04 | 0.03 | 0.02 | 0.02 | 0.02 |
| p-value 1 | | | ** | **** | **** | *** | **** | **** | **** | **** |
| p-value 2 | | | | | | | **** | **** | ** | ns |

TABLE 2-continued

Proliferation of cyst epithelia

| | | | anti-miR-17 | | | Control Oligonucleotide | | |
|---|---|---|---|---|---|---|---|---|
| | | | | | | #1 | #1 | #1 |
| Mean per Donor | PBS | Mock | 3 nM | 10 nM | 30 nM | 3 nM | 10 nM | 30 nM |
| Donor 5 mean | 1.00 | 0.99 | 0.89 | 0.64 | 0.42 | 1.11 | 0.92 | 0.88 |
| SEM | 0.09 | 0.10 | 0.06 | 0.06 | 0.04 | 0.12 | 0.07 | 0.05 |
| p-value 1 | | | ns | ns | *** | ns | ns | ns |
| p-value 2 | | | | | | **** | ** | ** |

In Vitro Cyst Formation

Human primary ADPKD cells were grown to 80% confluency and trypsinized using 1:10 dilution of trypsin in $Ca^{+2}$ and $Mg^{+2}$ free PBS. At day-one, cells were transfected using RNAiMAX in a six-well plate format. Treatment groups were as follows:

anti-miR-17 at doses of 1 nM, 5 nM, or 20 nM (n=3 for each dose)

five control oligonucleotides, each at a dose of 20 nM (n=3 for each control oligonucleotide)

mock-transfection with RNAiMAX (n=3)

PBS 24 hours after transfection, cells were trypsinized to single cell suspension, counted and plated in a 96-well plate at 4000 cells/well density in 130 μl of media plus Matrigel in a 4:5 ratio. Upon matrigel solidification, complete growth media was added to the well. Media was replenished every 72 hours until 8 days post-plating when the cyst size and number was measured.

Each well was inspected for cyst proliferation using an Olympus D8 light microscope. Images were recorded with an Olympus DP26 camera (Olympus Corporation) from 28 focal planes, 150 μm apart, down into the well (on the z-axis) as twenty-eight 24-bit color TIFF images at 2448-by-1920 pixels at 72 dpi. Each focal plane's image from each well was processed using a custom R script (R Core Team 2015 R: A language and environment for statistical computing. R Foundation for Statistical Computing, Vienna, Austria, found at www.R-project.org.) that used the EBImage Bioconductor package 15. This script detected cysts in an automated and reproducible manner and was applied to all matrigel assays in all donors. Briefly, each image was masked for artifacts, filtered through a high-pass Laplacian filter, and segmented with an adaptive threshold. Detected objects in the segmented images were further processed by pixel dilation, hole-filling, and by pixel erosion. Size, radius and eccentricity statistics on each segmented object were collected. Objects were filtered out if they had a mean radius less than or equal to 15 pixels, or were of a mean object radius greater than 200 pixels, or a coefficient of variation of the radius of greater than 0.2, or if the eccentricity of the detected object was greater than 0.75. Because cysts were often larger than the distance between focal planes, counting such cysts more than once was avoided. If a cyst object in one image fell within the same x- and y-coordinates of a neighboring image (e.g., one focal plane above on the z-axis), then this was counted as the same cyst. All images in each well were processed sequentially in this manner on the z-axis. Finally, each cyst's volume was estimated by multiplying the mean radius of the largest object by $4/37\,\pi r^3$, assuming each cyst is a sphere.

Results are shown in Table 3. The mean for each anti-miR-17 treatment group or control oligonucleotide treatment group is normalized to the mean for the mock treatment group. Standard error of the mean is shown. Statistical analysis was performed using Student's t-test for pairwise comparisons or Analysis of variance (ANOVA) followed by Tukey's post hoc test for multiple comparison. P values are as follows: * indicates P<0.05, indicates P<0.01, *indicates P<0.005, and ****indicates P<0.001. For anti-miR-17 treatment, P-value indicates significance relative to mock treatment. For control oligonucleotide treatment, two different P-values are shown, one indicating significance relative to mock treatment (P-value 1 in Table 3) and the other indicating significance relative to anti-miR-17 30 nM treatment (P-value 2 in Table 3).

Treatment with anti-miR-17 produced a dose-dependent reduction in the cyst count, relative to mock transfection treatment. Unlike treatment with anti-miR-17, the majority of control oligonucleotide treatments did not consistently reduce cyst count by a statistically significant amount.

As an example, treatment of cyst epithelial cultures from Donor 3 with 30 nM anti-miR-17 reduced cell proliferation by 63%, relative to mock transfection (P<0.0001), whereas treatment with control oligonucleotides did not consistently reduce cyst count by a statistically significant amount. Further, for cyst count from the same donor, a comparison of anti-miR-17 30 nM treatment to each of the three control treatments also reveals a statistically significant reduction in cell proliferation by anti-miR-17 treatment (P<0.0001).

TABLE 3

Cyst Count

| | | | Treatment | | | | | | |
|---|---|---|---|---|---|---|---|---|---|
| | | | | | Control Oligonucleotides | | | | |
| Mean Cyst Count Per Donor | PBS | Mock | anti-miR-17 | | | #1 | #2 | #3 | #4 | #5 |
| | | | 1 nM | 5 nM | 20 nM | 30 nM | 30 nM | 30 nM | 30 nM | 30 nM |
| Donor 3 mean | 0.85 | 1.00 | 0.86 | 0.65 | 0.37 | 0.79 | 1.11 | 0.90 | 0.53 | 0.86 |
| SEM | 0.04 | 0.02 | 0.04 | 0.03 | 0.05 | 0.05 | 0.02 | 0.06 | 0.03 | 0.05 |
| p-value 1 | | | ns | *** | **** | * | ns | ns | **** | ns |
| p-value 2 | | | | | | **** | **** | **** | ns | **** |
| Donor 4 mean | 1.22 | 1.00 | 0.69 | 0.46 | 0.24 | 1.08 | 1.02 | 0.88 | 0.44 | 0.75 |
| SEM | 0.04 | 0.07 | 0.01 | 0.06 | 0.03 | 0.06 | 0.09 | 0.07 | 0.05 | 0.04 |
| p-value 1 | | | * | **** | **** | ns | ns | ns | **** | ns |
| p-value 2 | | | | | | **** | **** | **** | ns | *** |

These data demonstrate that treatment with anti-miR-17 inhibits the proliferation of cysts derived from human ADPKD patients.

Example 5

Anti-miR-17 in the Pcy Model of PKD

Pcy mice bearing a mutation in Nphp3 spontaneously develop polycystic kidney disease, with a slower progression of disease than that observed in the Pkhd1/cre;Pkd2$^{F/F}$ mice. The Pcy model is used as a model of human PKD, as well as a model of the nephronophthisis/medullary cystic kidney disease (NPH/MCD) complex. A modified oligonucleotide complementary to miR-17 (anti-miR-17 compound) was tested in the Pcy mouse model. Wild-type mice were used as control mice. An oligonucleotide complementary to a miRNA unrelated to miR-17 was used as a treatment control for specificity (anti-miR-control). The anti-miR-17 compound was a fully phosphorothioated oligonucleotide 19 linked nucleosides in length (5'-CTGCACTGTAAGCACTTTG-3'; SEQ ID NO: 15), with DNA, 2'-MOE and S-cEt sugar moieties.

Pcy mice (CD1-pcylusm) were obtained from PreClinOmic. From four weeks of age, Pcy mice were treated once per week with anti-miR-17 (50 mg/kg via subcutaneous injection) or PBS, for a total of 26 doses. The anti-miR-17 group contained 12 mice, and the PBS control group contained 11 mice.

An additional control group included age-matched CD1 mice, obtained from Charles River Laboratories. CD1 mice were subcutaneously injected with PBS one per week, for a total of 26 weeks.

At the end of the 26 week treatment period, mice were sacrificed, and one kidney was extracted and weighed and the other processed for histological analysis. Blood urea nitrogen (BUN) and serum creatinine were measured.

For histological analysis, one kidney was perfused with cold PBS and 4% (wt/vol) paraformaldehyde and then harvested. Kidneys were fixed with 4% paraformaldehyde for 2 hours and then, embedded in paraffin for sectioning. Sagittal sections of kidneys were stained with hematoxylin and eosin (H&E). All image processing steps were automated and took place in freely available and open source software: An R1 script which used functions from the EBImage Bioconductor package2 and the ImageMagick3 suite of image processing tools. Kidney H&E images in Aperio SVS format were converted to TIFF images, and the first frame was retained for image analysis. First, the total kidney section area was calculated using image segmentation. Image segmentation was similarly used to find all internal structures including kidney cyst. A filter was applied to remove all objects less than a mean radius of three pixels. The cystic index is the image area associated with cysts divided by the total kidney areas. Cystic index was separately calculated for longitudinal and transverse kidney sections for each individual animal. Combined cystic index of individual animals were compared for each treatment groups.

Results from PBS-treated CD1 mice were used to provide a benchmark for each parameter (kidney weight/body weight ratio, cystic index, blood urea nitrogen and serum creatinine) in a non-disease model. As expected, treated CD1 mice did not exhibit any pathologies associated with PKD.

Figure 2B:
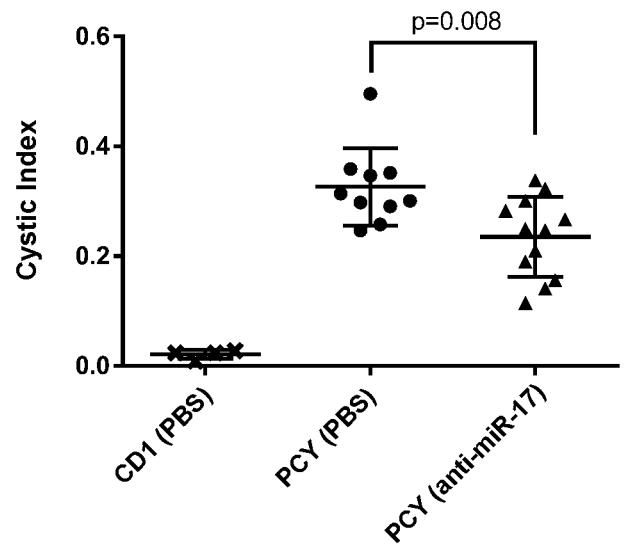

The mean ratio of kidney weight to body weight in the Pcy mice treated with anti-miR-17 was 19% lower than the mean ratio of kidney weight to body weight in the Pcy mice administered PBS only (p=0.0003) (FIG. 2A). Pcy mice treated with anti-miR-17 showed a mean 28% reduction in cyst index compared to Pcy mice administered PBS only (p=0.008) (FIG. 2B). No significant changes in BUN or serum creatinine were observed. P-values of 1-way ANOVA analysis following Dunnett's multiple comparison corrections are shown.

These data demonstrate, in an additional model of PKD, that treatment with anti-miR-17 leads to a reduction in kidney weight and cyst index.

What is claimed is:

1. A method of treating polycystic kidney disease comprising administering to a subject in need thereof a compound comprising a modified oligonucleotide consisting of 8 to 25 linked nucleosides, wherein the nucleobase sequence of the modified oligonucleotide is complementary to miR-17, wherein the nucleobase sequence of the modified oligonucleotide comprises the nucleobase sequence 5'-GCACTTTG-3' (SEQ ID NO: 3), wherein each T in the nucleobase sequence is independently selected from a T and a U, wherein the compound consists of the modified oligonucleotide, and wherein the polycystic kidney disease is autosomal dominant polycystic kidney disease.

2. The method of claim 1 wherein the subject has been diagnosed as having polycystic kidney disease prior to administering the modified oligonucleotide.

3. The method of claim 1, wherein the subject has increased total kidney volume.

4. The method of claim 1, wherein the subject has hypertension.

5. The method of claim 1, wherein the subject has impaired kidney function.

6. The method of claim 3, wherein the total kidney volume is height-adjusted kidney volume.

7. The method of claim 1, wherein the nucleobase sequence of the modified oligonucleotide is at least 90% complementary, is at least 95% complementary, or is 100% complementary to the nucleobase sequence of miR-17 (SEQ ID NO: 1).

8. The method of claim 1, wherein the modified oligonucleotide consists of 8, 9, 10, 11 or 12 linked nucleosides.

9. The method of claim 1, wherein the modified oligonucleotide consists of 12, 13, 14, 15, 16, 17, 18, 19, 20, 21, 22, 23, 24, or 25 linked nucleosides.

10. The method of claim 1, wherein the modified oligonucleotide consists of 15, 16, 17, 18, 19, 20, 21, or 22 linked nucleosides.

11. The method of claim 1, wherein the modified oligonucleotide consists of 17, 18, 19, 20, 21, 22, or 23 linked nucleosides.

12. The method of claim 1, wherein the modified oligonucleotide comprises at least one modified nucleoside.

13. The method of claim 12, wherein the modified nucleoside is selected from an S-cEt nucleoside, a 2'-O-methoxyethyl nucleoside, and an LNA nucleoside.

14. The method of claim 1, wherein each internucleoside linkage of the modified oligonucleotide is a modified internucleoside linkage.

15. The method of claim 14, wherein the modified internucleoside linkage is a phosphorothioate internucleoside linkage.

* * * * *

SEQUENCE LISTING

<160> NUMBER OF SEQ ID NOS: 32

<210> SEQ ID NO 1
<211> LENGTH: 23
<212> TYPE: RNA
<213> ORGANISM: Homo sapiens

<400> SEQUENCE: 1
caaagugcuu acagugcagg uag                                               23

<210> SEQ ID NO 2
<211> LENGTH: 84
<212> TYPE: RNA
<213> ORGANISM: Homo sapiens

<400> SEQUENCE: 2
gucagaauaa ugucaaagug cuuacagugc agguagugau augugcaucu acugcaguga       60
aggcacuugu agcauuaugg ugac                                              84

<210> SEQ ID NO 3
<211> LENGTH: 8
<212> TYPE: DNA
<213> ORGANISM: Artificial Sequence
<220> FEATURE:
<223> OTHER INFORMATION: modified oligonucleotide
<220> FEATURE:
<221> NAME/KEY: misc_feature
<222> LOCATION: (1)..(8)
<223> OTHER INFORMATION: T is independently selected from a T and a U

<400> SEQUENCE: 3 gcactttg                                                                 8

<210> SEQ ID NO 4
<211> LENGTH: 8
<212> TYPE: DNA
<213> ORGANISM: Artificial Sequence
<220> FEATURE:
<223> OTHER INFORMATION: modified oligonucleotide
<220> FEATURE:
<221> NAME/KEY: misc_feature
<222> LOCATION: (1)..(8)
<223> OTHER INFORMATION: T is independently selected from a T and a U

<400> SEQUENCE: 4 agcacttt                                                                 8

<210> SEQ ID NO 5
<211> LENGTH: 9
<212> TYPE: DNA
<213> ORGANISM: Artificial Sequence
<220> FEATURE:
<223> OTHER INFORMATION: modified oligonucleotide
<220> FEATURE:
<221> NAME/KEY: misc_feature
<222> LOCATION: (1)..(9)
<223> OTHER INFORMATION: T is independently selected from a T and a U

<400> SEQUENCE: 5 agcactttg                                                                9

<210> SEQ ID NO 6
<211> LENGTH: 10
<212> TYPE: DNA
<213> ORGANISM: Artificial Sequence
<220> FEATURE:
<223> OTHER INFORMATION: modified oligonucleotide

```
<220> FEATURE:
<221> NAME/KEY: misc_feature
<222> LOCATION: (1)..(10)
<223> OTHER INFORMATION: T is independently selected from a T and a U

<400> SEQUENCE: 6
aagcactttg                                                          10

<210> SEQ ID NO 7
<211> LENGTH: 11
<212> TYPE: DNA
<213> ORGANISM: Artificial Sequence
<220> FEATURE:
<223> OTHER INFORMATION: modified oligonucleotide
<220> FEATURE:
<221> NAME/KEY: misc_feature
<222> LOCATION: (1)..(11)
<223> OTHER INFORMATION: T is independently selected from a T and a U

<400> SEQUENCE: 7
taagcacttt g                                                        11

<210> SEQ ID NO 8
<211> LENGTH: 12
<212> TYPE: DNA
<213> ORGANISM: Artificial Sequence
<220> FEATURE:
<223> OTHER INFORMATION: modified oligonucleotide
<220> FEATURE:
<221> NAME/KEY: misc_feature
<222> LOCATION: (1)..(12)
<223> OTHER INFORMATION: T is independently selected from a T and a U

<400> SEQUENCE: 8
gtaagcactt tg                                                       12

<210> SEQ ID NO 9
<211> LENGTH: 13
<212> TYPE: DNA
<213> ORGANISM: Artificial Sequence
<220> FEATURE:
<223> OTHER INFORMATION: modified oligonucleotide
<220> FEATURE:
<221> NAME/KEY: misc_feature
<222> LOCATION: (1)..(13)
<223> OTHER INFORMATION: T is independently selected from a T and a U

<400> SEQUENCE: 9
tgtaagcact ttg                                                      13

<210> SEQ ID NO 10
<211> LENGTH: 14
<212> TYPE: DNA
<213> ORGANISM: Artificial Sequence
<220> FEATURE:
<223> OTHER INFORMATION: modified oligonucleotide
<220> FEATURE:
<221> NAME/KEY: misc_feature
<222> LOCATION: (1)..(14)
<223> OTHER INFORMATION: T is independently selected from a T and a U

<400> SEQUENCE: 10
ctgtaagcac tttg                                                     14

<210> SEQ ID NO 11
<211> LENGTH: 15
<212> TYPE: DNA
<213> ORGANISM: Artificial Sequence
<220> FEATURE:
```

```
<223> OTHER INFORMATION: modified oligonucleotide
<220> FEATURE:
<221> NAME/KEY: misc_feature
<222> LOCATION: (1)..(15)
<223> OTHER INFORMATION: T is independently selected from a T and a U

<400> SEQUENCE: 11
actgtaagca ctttg                                                    15

<210> SEQ ID NO 12
<211> LENGTH: 16
<212> TYPE: DNA
<213> ORGANISM: Artificial Sequence
<220> FEATURE:
<223> OTHER INFORMATION: modified oligonucleotide
<220> FEATURE:
<221> NAME/KEY: misc_feature
<222> LOCATION: (1)..(16)
<223> OTHER INFORMATION: T is independently selected from a T and a U

<400> SEQUENCE: 12
cactgtaagc actttg                                                   16

<210> SEQ ID NO 13
<211> LENGTH: 17
<212> TYPE: DNA
<213> ORGANISM: Artificial Sequence
<220> FEATURE:
<223> OTHER INFORMATION: modified oligonucleotide
<220> FEATURE:
<221> NAME/KEY: misc-_feature
<222> LOCATION: (1)..(17)
<223> OTHER INFORMATION: T is independently selected from a T and a U

<400> SEQUENCE: 13
gcactgtaag cactttg                                                  17

<210> SEQ ID NO 14
<211> LENGTH: 18
<212> TYPE: DNA
<213> ORGANISM: Artificial Sequence
<220> FEATURE:
<223> OTHER INFORMATION: modified oligonucleotide
<220> FEATURE:
<221> NAME/KEY: misc_feature
<222> LOCATION: (1)..(18)
<223> OTHER INFORMATION: T is independently selected from a T and a U

<400> SEQUENCE: 14
tgcactgtaa gcactttg                                                 18

<210> SEQ ID NO 15
<211> LENGTH: 19
<212> TYPE: DNA
<213> ORGANISM: Artificial Sequence
<220> FEATURE:
<223> OTHER INFORMATION: modified oligonucleotide
<220> FEATURE:
<221> NAME/KEY: misc_feature
<222> LOCATION: (1)..(19)
<223> OTHER INFORMATION: T is independently selected from a T and a U

<400> SEQUENCE: 15
ctgcactgta agcactttg                                                19

<210> SEQ ID NO 16
<211> LENGTH: 20
<212> TYPE: DNA
<213> ORGANISM: Artificial Sequence
```

```
<220> FEATURE:
<223> OTHER INFORMATION: modified oligonucleotide
<220> FEATURE:
<221> NAME/KEY: misc_feature
<222> LOCATION: (1)..(20)
<223> OTHER INFORMATION: T is independently selected from a T and a U

<400> SEQUENCE: 16
cctgcactgt aagcactttg                                                 20

<210> SEQ ID NO 17
<211> LENGTH: 21
<212> TYPE: DNA
<213> ORGANISM: Artificial Sequence
<220> FEATURE:
<223> OTHER INFORMATION: modified oligonucleotide
<220> FEATURE:
<221> NAME/KEY: misc_feature
<222> LOCATION: (1)..(21)
<223> OTHER INFORMATION: T is independently selected from a T and a U

<400> SEQUENCE: 17
acctgcactg taagcactttt g                                              21

<210> SEQ ID NO 18
<211> LENGTH: 22
<212> TYPE: DNA
<213> ORGANISM: Artificial Sequence
<220> FEATURE:
<223> OTHER INFORMATION: modified oligonucleotide
<220> FEATURE:
<221> NAME/KEY: misc_feature
<222> LOCATION: (1)..(22)
<223> OTHER INFORMATION: T is independently selected from a T and a U

<400> SEQUENCE: 18
cacctgcact gtaagcactt tg                                              22

<210> SEQ ID NO 19
<211> LENGTH: 23
<212> TYPE: DNA
<213> ORGANISM: Artificial Sequence
<220> FEATURE:
<223> OTHER INFORMATION: modified oligonucleotide
<220> FEATURE:
<221> NAME/KEY: misc_feature
<222> LOCATION: (1)..(23)
<223> OTHER INFORMATION: T is independently selected from a T and a U

<400> SEQUENCE: 19
ctacctgcac tgtaagcact ttg                                             23

<210> SEQ ID NO 20

<400> SEQUENCE: 20

000

<210> SEQ ID NO 21
<211> LENGTH: 23
<212> TYPE: RNA
<213> ORGANISM: Homo sapiens

<400> SEQUENCE: 21
uaaagugcuu auagugcagg uag                                             23

<210> SEQ ID NO 22
<211> LENGTH: 23
```

```
<212> TYPE: RNA
<213> ORGANISM: Homo sapiens

<400> SEQUENCE: 22
caaagugcuc auagugcagg uag                                              23

<210> SEQ ID NO 23
<211> LENGTH: 23
<212> TYPE: RNA
<213> ORGANISM: Homo sapiens

<400> SEQUENCE: 23
caaagugcug uucgugcagg uag                                              23

<210> SEQ ID NO 24
<211> LENGTH: 23
<212> TYPE: RNA
<213> ORGANISM: Homo sapiens

<400> SEQUENCE: 24
aaaagugcuu acagugcagg uag                                              23

<210> SEQ ID NO 25
<211> LENGTH: 21
<212> TYPE: RNA
<213> ORGANISM: Homo sapiens

<400> SEQUENCE: 25
uaaagugcug acagugcaga u                                                21

<210> SEQ ID NO 26
<211> LENGTH: 23
<212> TYPE: RNA
<213> ORGANISM: Homo sapiens

<400> SEQUENCE: 26
uaaggugcau cuagugcaga uag                                              23

<210> SEQ ID NO 27
<211> LENGTH: 23
<212> TYPE: RNA
<213> ORGANISM: Homo sapiens

<400> SEQUENCE: 27
uaaggugcau cuagugcagu uag                                              23

<210> SEQ ID NO 28
<211> LENGTH: 23
<212> TYPE: RNA
<213> ORGANISM: Homo sapiens

<400> SEQUENCE: 28
ugugcaaauc uaugcaaaac uga                                              23

<210> SEQ ID NO 29
<211> LENGTH: 23
<212> TYPE: RNA
<213> ORGANISM: Homo sapiens

<400> SEQUENCE: 29
ugugcaaauc caugcaaaac uga                                              23

<210> SEQ ID NO 30
```

```
<211> LENGTH: 22
<212> TYPE: RNA
<213> ORGANISM: Homo sapiens

<400> SEQUENCE: 30
cauugcacuu gucucggucu ga                                              22

<210> SEQ ID NO 31
<211> LENGTH: 22
<212> TYPE: RNA
<213> ORGANISM: Homo sapiens

<400> SEQUENCE: 31
uauugcacuu gucccggccu gu                                              22

<210> SEQ ID NO 32
<211> LENGTH: 22
<212> TYPE: RNA
<213> ORGANISM: Homo sapiens

<400> SEQUENCE: 32
aauugcacgg uauccaucug ua                                              22
```